United States Patent [19]
Goldin et al.

[11] Patent Number: 5,312,928
[45] Date of Patent: May 17, 1994

[54] CALCIUM CHANNEL ANTAGONISTS AND METHODOLOGY FOR THEIR IDENTIFICATION

[75] Inventors: Stanley M. Goldin, Lexington; Kazumi Kobayashi, Arlington; Andrew G. Knapp, Salem; Lee Margolin; Subbarao Katragadda, both of Belmont; Deborah Daly, Melrose; Lain-Yen Hu, Waltham; N. Laxma Reddy, Malden, all of Mass.

[73] Assignee: Cambridge Neuroscience, Cambridge, Mass.

[21] Appl. No.: 654,104

[22] Filed: Feb. 11, 1991

[51] Int. Cl.⁵ ............... C07D 209/20; A61K 31/405
[52] U.S. Cl. ................................ 548/495; 548/494
[58] Field of Search ............... 548/495, 494; 514/415

[56]  References Cited
U.S. PATENT DOCUMENTS 4,925,664  5/1990  Jackson et al. .................... 424/537
4,950,739  8/1990  Cherksey et al. ................. 838/380

FOREIGN PATENT DOCUMENTS 0395357 10/1990 European Pat. Off. .

OTHER PUBLICATIONS

Jasys, V. J. et al., "Isolation, Structure Elucidation, and Synthesis of Novel Hydroxylamine-Containing Polyamines from the Venom of the *Agelenopsis aperta* Spider", J. Am. Chem. Soc., 112:6696–6704 (1990).

(List continued on next page.)

Primary Examiner—David B. Springer
Attorney, Agent, or Firm—Fish & Richardson

[57]  ABSTRACT

A substantially pure compound of the formula:

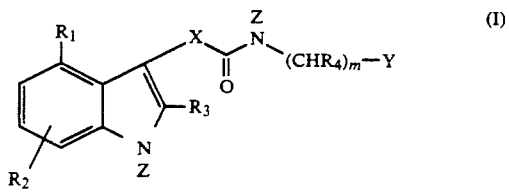

wherein
each of $R_1$ and $R_2$, independently, is H, $CH_3$, $CF_3$, F, Cl, Br, I, OH, $OCH_3$, $OCF_3$, SH, $SCH_3$, $NH_2$, $N_3$, $NO_2$, CN, COOH, $CONH_2$, $CH_2CONH_2$, or $SO_2NH_2$;
$R_3$ is H, $CH_3$, COOH, $CONH_2$, or COOR where R is $C_{1-4}$ alkyl;
each $R_4$, independently, is H or $C_{1-6}$ alkyl;
X is $CH_2$, $CH_2CH_2$, CH=CH, or $CH_2CH_2CH_2$;

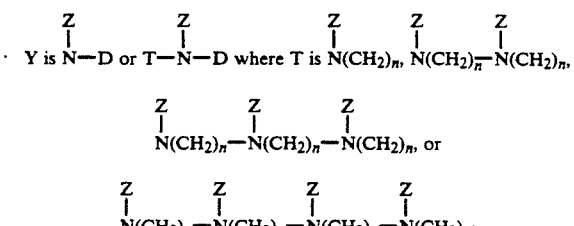

each Z, independently, is H, $CH_3$, or Q where Q is a hydrophobic acyl, benzoyl, phenacetyl, benzyloxycarbonyl, alkoxycarbonyl, or N-methyl-dihydropyridine-3-carbonyl linked to N by an amide bond which is cleavable by an endogenous central nervous system enzyme;
D is H or

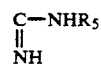

where $R_5$ is H or $C_{1-4}$ alkyl;
m is an integer from 2 to 12, inclusive; and
each n, independently, is an integer from 2 to 12, inclusive; a therapeutic composition including such compound; and a process for identifying calcium channel antagonists.

19 Claims, 11 Drawing Sheets

OTHER PUBLICATIONS

Skinner, W. S. et al., "Chemical Characterization of Acylpolyamine Toxins from Venom of a Trap-Door Spider and Two Tarantulas", Toxicon, 28:541-546 (1990).

Adams, M. E. et al., "Structures and Biological Acitivities of Three Synaptic Antagonists From Orb Weaver Spider Venom", Biochem. Biophys. Res. Comm., 148:678-683 (1987).

Skinner, W. S. et al., "Purification and Characterization of Two Classes of Neurotoxins from the Funnel Web Spider, *Agelenopsis aperta*", J. Biol. Chem, 264:2150-2155 (1988).

Llinas, R. et al., "Blocking and isolation of a Calcium Channel From Neurons in Mammals and Cephalopods Utilizing a Toxin Fraction (FTX) From Funnel-Web Spider Poison", Proc. Natl. Acad. Sci., USA, 86:1689-1693 (1989).

Adams, M. E. et al., "Two Classes of Channel-Specific Toxins From Funnel Web Spider Venom", J. Chem. Physiol A., 164:333-342 (1989).

CALCIUM CHANNEL ANTAGONISTS AND METHODOLOGY FOR THEIR IDENTIFICATION

BACKGROUND OF THE INVENTION

This invention was made in the course of work supported in part by the U.S. Government, which has certain rights in the invention. The invention relates to calcium channel antagonists, methodology for their identification, and their therapeutic applications.

Calcium channels are protein molecules containing pores extending through the membranes of cells or cellular organelles, which reversibly open and close, thus regulating the passage of $Ca^{++}$ ions into and out of the cell or organelle. The type of calcium channels termed "voltage-sensitive" open and close in response to changes in the voltage difference across the cellular membrane. There are at least three known subclasses of voltage-sensitive calcium channels ("L-type", "N-type", and "T-type") that differ in their pharmacology, location in neuronal and non-neuronal tissues, and physiological properties [Nowycky, M. C. et al. (1985) Nature 316:440; Bean, B. P. et al. (1989) Ann. Rev. Physiol. 51:367].

L-type channels are characterized by (1) "high threshold" for activation, i.e., a strong depolarization of the cell membrane in which they are located is required to open such channels; (2) large "single channel conductance", i.e., each channel, when opened, can allow the passage of $Ca^{+2}$ ions at a relatively high rate; (3) greater permeability to $Ba^{+2}$ than $Ca^{+2}$; and, of particular note, (4) sensitivity to high potency block by the dihydropyridine class of calcium channel antagonists such as nimodipine and nifedipine (characteristically the $IC_{50}$ values for L-channel block by these drugs are below 1 $\mu M$). In most cases, the calcium "action potentials" mediated by L-type channels under normal physiological circumstances is of relatively long duration, typically no less than 100 msec.

L-type channels in the cardiovascular system are the sites of action of several therapeutically important classes of calcium antagonists: the aforementioned dihydropyridines (of particular significance, nifedipine), phenylalkylamines (e.g., verapamil), and benzothiazepines (e.g., diltiazem) [Schwartz, A. et al. (1988) Amer. J. Cardiol. 62, 3G]. These drugs have been successfully and widely employed for the treatment of hypertension, angina pectoris, cardiac arrhythmias, and congestive heart failure [Katzung, W. B. (1987) Basic and Clinical Pharmacology, 3rd Ed., Lange Medical Books, Norwalk, Conn., Chaps. 10–13].

The dihydropyridine calcium antagonist, nimodipine, acts both as a cerebral vasodilator [Wong, M. C. W. and Haley, E. C. Jr. (1989) Stroke 24:31], and as a blocker of calcium entry into neurons [Scriabine, A. (1990) Adv. in Neurosurg. 18:173; Nuglisch, J. et al. (1990) J. Cereb. Blood Flow and Metab. 10: 654]. Modest improvement in the outcome of stroke has been observed in clinical trials of nimodipine [Gelmers, H. J. et al. (1988) N. Eng. J. Med. 318:203].

While there are significant cardiovascular side effects, nimodipine may find a role in the chronic treatment of stroke and other neurological disorders. Blockade of L-type channels in brain neurons appears to account, at least in part, for the therapeutic effects of nimodipine in stroke and other forms of ischemia, epilepsy, and in animal models of dementia [Scriabine, A. (1990) ibid; Deyo, R. A. et al. (1989) Science 243:809].

Nimodipine is currently undergoing clinical trials for use in therapy of Alzheimer's disease.

T-type channels are characterized by a relatively low threshold for activation, and rapidly inactivate when activated by strong depolarizations. They are relatively insensitive to dihydropyridines. Their low threshold of activation makes them well suited for participation in pacemaking, and they accordingly appear to play a major role in regulating the beating of the heart.

N-type channels are high threshold channels which are most appropriately described as dihydropyridine-insensitive but blocked by interaction with the cone snail toxin omega-conotoxin. Qualitatively, as a class, N-type channels inactivate somewhat more rapidly than L-type channels. Because there is overlap between L- and N-type channel classes in this regard, differences in inactivation kinetics do not constitute a defining characteristic.

Recently, another class of calcium channels has been reported [Sah, D. W. Y. et al. (1989) Soc. Neurosci. Abs. 15, $\mu3$]. This class, herein termed "R-type channels", may be characterized as high-threshold calcium channels which are relatively resistant to block by dihydropyridines and omega-conotoxin. Such channels are found in a wide variety of neurons, and are particularly abundant in cerebellar Purkinje cells. R-type channels may play a role in synaptic transmission and other processes that depend on calcium entry but are not sensitive to these blockers.

SUMMARY OF THE INVENTION

In one aspect, the invention provides substantially pure compounds of the formula:

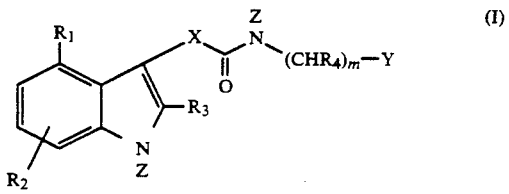

wherein
each of $R_1$ and $R_2$, independently, is H, $CH_3$, $CF_3$, F, Cl, Br, I, OH, $OCH_3$, $OCF_3$, SH, $SCH_3$, $NH_2$, $N_3$, $NO_2$, CN, COOH, $CONH_2$, $CH_2CONH_2$, or $SO_2NH_2$;

$R_3$ is H, $CH_3$, COOH, $CONH_2$, or COOR where R is $C_{1-4}$ alkyl;

each $R_4$, independently, is H or $C_{1-6}$ alkyl;

X is $CH_2$, $CH_2CH_2$, CH=CH, or $CH_2CH_2CH_2$;

Y is N—D or T—N—D where T is $\overset{Z}{N}(CH_2)_n$, $\overset{Z}{N}(CH_2)_{\overline{n}}\overset{Z}{N}(CH_2)_n$,

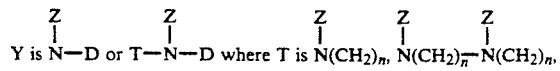

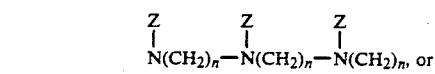

each Z, independently, is H, $CH_3$, or Q where Q is a hydrophobic acyl, benzoyl, phenacetyl, benzyloxycarbonyl, alkoxycarbonyl, or N-methyl-dihydropyridine-3-carbonyl, Q being linked to N (the N to which it is immediately adjacent) by an amide bond which is cleavable by an endogenous central nervous system enzyme;

D is H or

where $R_5$ is H or $C_{1-4}$ alkyl;

m is an integer from 2 to 12, inclusive; and each n, independently, is an integer from 2 to 12, inclusive.

A "substantially pure compound" or "substantially pure preparation of a compound", as those terms are used herein, means that the claimed compound is provided as a composition of which less than five percent by weight (and potentially as little as zero percent) consists of other organic molecules with which the designated compound is naturally associated.

The terms hydrophobic acyl, benzoyl, phenacetyl, benzyloxycarbonyl, and alkoxycarbonyl, as used herein, refer to moieties of those classifications which repel water. For example, the alkyl chains in fatty acids are hydrophobic, imparting the tendency for such compounds to leave the water phase and associate with other hydrophobic structures such as the lipid phase of cellular membranes. This hydrophobicity enables such compounds to penetrate the hydrophobic blood-brain barrier, while a less hydrophobic compound could not. The term "blood-brain barrier" refers to a boundary between the peripheral and central nervous systems, comprising a permeability barrier to the passive diffusion of substances from the bloodstream into various regions of the systems.

Preferably, each of $R_1$ and $R_2$, independently, is H, $CH_3$, $CF_3$, F, Cl, Br, I, OH, $NH_2$, $NO_2$, $CONH_2$, or $SO_2NH_2$; $R_3$ is H, $CH_2$, or $CONH_2$; $R_4$ is H, $CH_3$, $C_2H_5$, $C_3H_7$, or $C_4H_9$; X is $CH_2$, CH=CH, $CH_2CH_2$, or $CH_2CH_2CH_2$; and Z is H or $CH_3$.

In other preferred embodiments, $R_1$ is OH, each of $R_2$, $R_3$, $R_4$, and Z is H, m is 3 or 5,

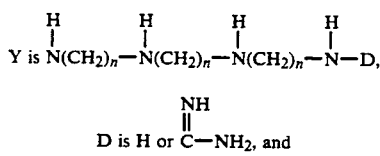

D is H or $\overset{NH}{\underset{\parallel}{C}}-NH_2$, and each n, independently, is 3, 4, or 5. Alternatively, m is 8, 10, or 12; and Y is T-$NH_2$ or

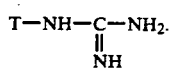

Also preferred is the compound of formula I, wherein Q is acyl or benzoyl linked to N by an amide bond; or alternatively, wherein Q is phenacetyl, benzyloxycarbonyl, or alkoxycarbonyl linked to N by an amide bond; or alternatively, wherein Q is N-methyl dihydropyridine-3-carbonyl linked to N by an amide bond. In each case, Q is a hydrophobic moiety which serves to mask the charged amine, permitting the compound to cross the blood-brain barrier. After the compound crosses the blood-brain barrier, the amide bond can be cleaved by endogenous enzymes in the brain, releasing active compound.

It is further preferred to provide the compound of formula I, wherein each of $R_3$ and $R_4$ is H; X is $CH_2$; Y is T-$NH_2$; m is 3, 4, or 5; and each n, independently, is 3, 4, or 5. More preferred are those compounds wherein $R_1$ is OH, $R_2$ is H, and each Z is H, and particularly more preferred are those wherein m is 3 or 5 and each n, independently, is 3 or 5. Four of the most preferred compounds have the formulas set forth below:

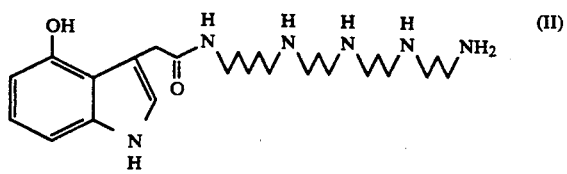

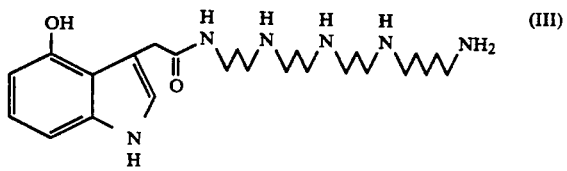

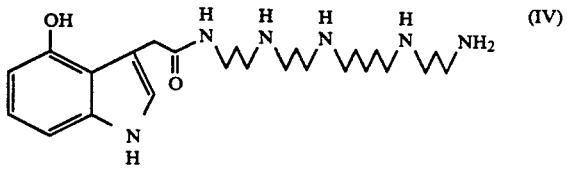

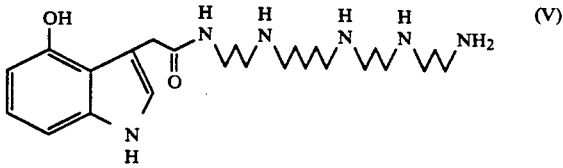

It is preferable that the compound of formula I be a calcium channel antagonist, that is, it is capable of blocking or otherwise reducing the extent or duration, or both, of calcium entry through voltage-sensitive calcium channels. More preferably, the compound is an antagonist of R-type, L-type or T-type calcium channels in mammalian neuronal cells, (such cells being either of the central nervous system or of peripheral nerves), or in mammalian cardiovascular cells. R-type, L-type or T-type calcium channels are defined in "Background of the Invention" above. The term "cardiovascular cells" refers to cells integral to the function of the cardiovascular system, including, of salient importance:

(a) smooth muscle cells lining the walls of the blood vessels. Contraction of these cells reduces blood vessel diameter and thus contributes to elevation of blood pressure. Calcium channel antagonists acting at L-type channels on such cells will relax the cells and dilate blood vessels, thus contributing to the reduction of blood pressure.

(b) cardiac muscle cells responsible for the pumping action of the heart.

(c) cells of the cardiac conduction network (Purkinje fibers and internodal tract) responsible for conducting the electrical impulses which trigger the contraction of cardiac muscle.

(d) cells of the SA and AV nodes, which control, respectively, the rate of the heartbeat and the timing of the delay between contraction of the atria and the ventricles.

It is further preferable that the compound of formula I be a calcium channel antagonist capable of reversibly blocking calcium channels. By this is meant that the antagonist functions by nonpermanently (i.e., noncovalently) binding to the protein molecules which constitute such channels. Reversibility is indicated by the disappearance of the blocking effect when excess antagonist is removed from the cells, e.g., by washing the cells or by gradual metabolism of the compound.

It is yet further preferable that the compound of formula I be a calcium channel antagonist which blocks calcium channels to a greater degree than it blocks neurotransmitter-activated channels, voltage-sensitive sodium channels and potassium channels: i.e., its $IC_{50}$ for calcium channels is lower (preferably substantially lower) than that for such neurotransmitter-activated, sodium and potassium channels.

Another aspect of the invention features a pharmaceutical composition for the treatment of a condition involving excessive or inappropriate calcium influx into cells. The composition includes a therapeutically-effective amount of a calcium channel antagonist of formula I, in a pharmaceutically-acceptable vehicle. The term "therapeutically-effective amount" is defined below.

Preferably, the pharmaceutical composition is for the treatment of a condition involving excessive or inappropriate calcium influx into neuronal cells, including such conditions as stroke, brain trauma, Alzheimer's disease, multiinfarct dementia, other classes of dementia, Korsakoff's disease, a neuropathy caused by a viral infection of the brain or spinal cord (e.g., the HIV virus causing AIDS), amyotrophic lateral sclerosis, convulsions, seizures, Huntington's disease, amnesia, or damage to the nervous system resulting from reduced oxygen supply, poisons, or other toxic substances. It is particularly preferable that the compound be capable of crossing the blood-brain barrier of a mammal.

The pharmaceutical composition of the invention may also be used for the treatment of a condition involving excessive or inappropriate calcium influx into cardiovascular cells, including such conditions as cardiac arrhythmia, angina pectoris, hypoxic damage to the cardiovascular system, ischemic damage to the cardiovascular system, myocardial infarction, or congestive heart failure.

Also within the invention is a substantially pure preparation (as that term is defined above) of a compound, which compound is present in a spider of one of the following families: Pisauridae, Theraphosidae, Ctenizidae, Atypidae, Argyronetidae, Oxypodidae, Lycosidae, Gnaphosidae, Clubionidae, Ctenidae, Heteropodidae, Thomisidae, or Salticidae (preferably Pisauridae), and which functions as a calcium channel antagonist. Preferably, the compound is not a polypeptide, but rather is a molecule such as a polyamine, i.e., a compound having two or more amine groups, and is present in a spider of genus Dolomedes (e.g., of species okefenokiensis) or genus Phoneutria, which includes spiders with particularly potent venom.

Also within the invention is a process for obtaining a preparation having calcium channel antagonist activity. The process includes the steps of selecting a spider which indigenously does not employ webs to capture its prey (e.g., a spider of one of the families listed above), collecting venom from the spider (e.g., by standard methods familiar to those in the art), fractionating the venom, and identifying a fraction of the venom which shows calcium channel-blocking activity. Fractionation of the venom can be accomplished by any of a number of standard biochemical methods, including HPLC, gel filtration, affinity chromatography, and ion exchange chromatography. Identification of biologically-active fractions can be conveniently done by means of an assay such as one of those described herein.

One such assay, termed the "microscreen assay", is useful in general for identifying a substance (e.g., a constituent of spider venom) which affects cross-membrane transport of a molecule or an ion such as $Ca^{++}$ or $Na^+$. It includes the steps of (in a final reaction volume not exceeding 50 microliters (preferably not greater than 25 microliters, and more preferably 10 microliters or less): providing a preparation of cells, organelles or membrane vesicles (preferably from a mammalian source); adding to the preparation a given amount of a given molecule or an ion, which molecule or ion is identifiably labeled; and comparing (a) the level of labeled molecules or ions taken up by the cells, organelles or membrane vesicles in the presence of the substance being tested, to (b) the level taken up by the cells, organelles or membrane vesicles in the absence of the substance. Organelles useful in such an assay might include endoplasmic reticulum, sarcoplasmic reticulum, and neurosecretory structures such as synaptosomes, while the term "membrane vesicles" refers to sealed, semipermeable structures bounded by cell membranes, which are artificially created by the processing of cells or material derived from cells, using methods well known in the art. Membrane vesicles are typically produced by procedures which may include sonication, homogenization, osmotic shock, mild detergent treatment, or various combinations thereof.

When certain fragile cells are used to practice this process, it is preferred that they be attached to a solid support, e.g., microcarrier beads such as Sigma Glass Microcarrier Beads or Cultispher-G ™ Macroporous Gelatin Microcarriers, or to a microporous support, e.g., a microporous filter such as Millipore HA filters or Whatman glass fiber filters.

Also within the invention is a calcium channel antagonist identified by means of the process of the invention described above, including but not limited to one identified from spider venom.

The calcium channel antagonists of the invention are useful for the treatment of neurological and cardiovascular conditions characterized by excessive influx of calcium ions. Certain of these calcium channel antagonists are effective in blocking both L- and R-type calcium channels, and thus have a broader spectrum of action than known drugs which primarily act on only a single type of channel. Furthermore, those calcium channel antagonists of the invention which show specificity for R-type over L-type channels may be effective in treatment of neurological disorders, while producing fewer cardiovascular side effects than certain currently available antagonists which act primarily on L-type channels. The use of venom from spiders which indigenously do not employ webs to capture their prey was based on the theory that their venom must act more rapidly and therefore may be a particularly desirable source for potent drugs. The successful isolation of potent and specific calcium channel antagonists from such venom demonstrates the advantage of this approach.

Other features and advantages of the invention will be apparent from the following detailed description, and from the claims.

DETAILED DESCRIPTION

The drawings will first be described.

DRAWINGS

FIG. 5 also illustrates absorbance at 254 nm versus time.

PURIFICATION OF DOC1 AND DOC3 FROM SPIDER VENOM

*Dolomedes okefenokiensis* spiders were collected in Northern Florida and milked by The Spider Pharm (Arizona) using electro-stimulation, producing a crude venom preparation that was supplied to the inventors as a frozen solution. The venom was thawed on ice, aliquoted into appropriate portions, and kept at $-80°$ C. until use.

Both DOC1 and DOC3 were purified by high performance liquid chromatography (HPLC), using a Beckman System Gold HPLC system. As described below, two protocols were followed. The first one led to the discovery of compounds termed DOC1 and DOC3, and the second one was subsequently used as a routine procedure for large scale preparation of the compounds.

(1) INITIAL PURIFICATION FOR SCREENING

(a) Identification of DOC Fraction

Figure 1:
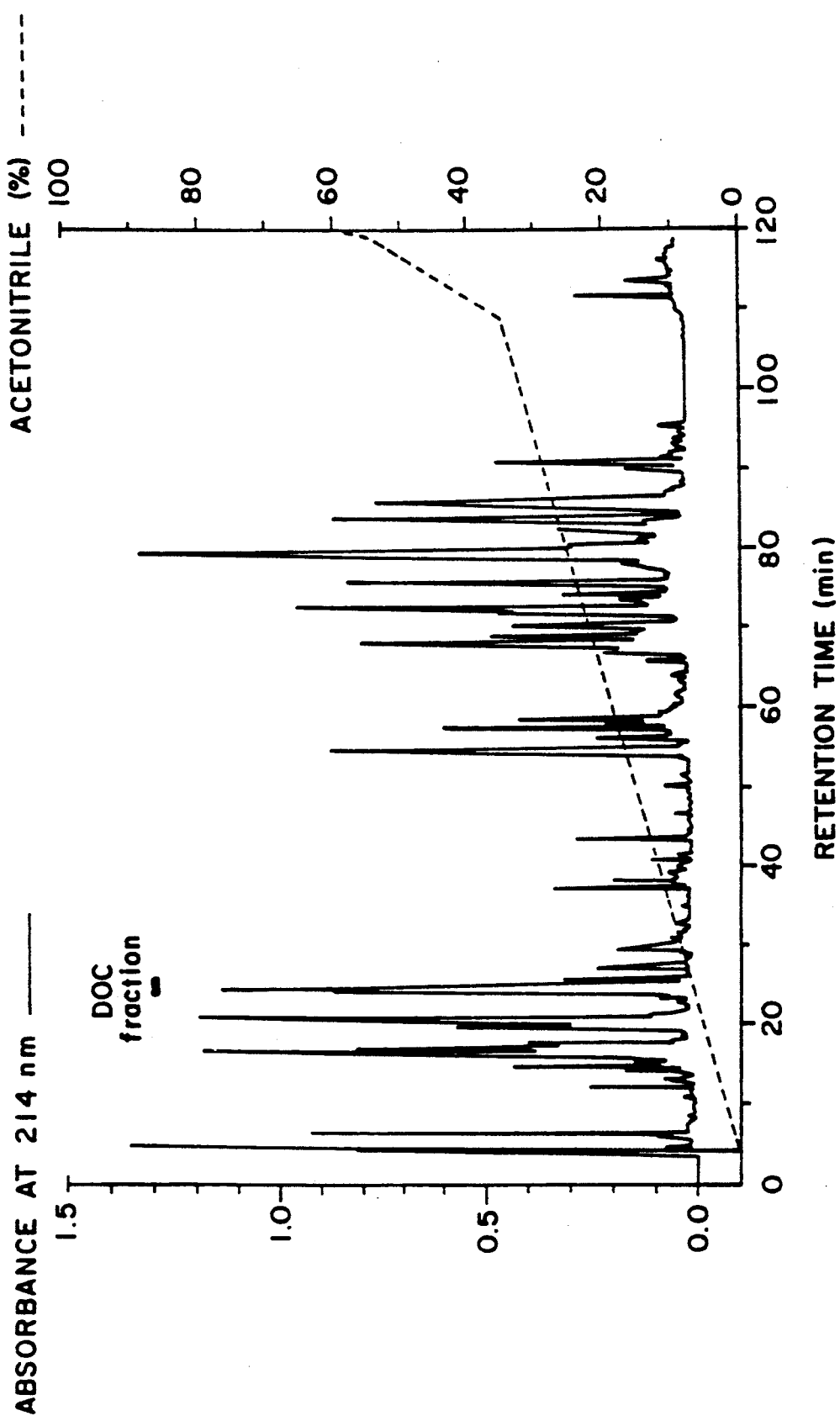
FIGS. 1-5 are elution profiles of *Dolomedes okefenokiensis* venom fractionated by reverse phase high performance liquid chromatography (HPLC), illustrating absorbance at 214 nm versus time.

Frozen crude venom (40 $\mu$l) was thawed on ice and mixed with 210 $\mu$l of ice-cold 0.1% trifluoroacetic acid (TFA) in $H_2O$. The solution was centrifuged at room temperature for 5 min. at 13,000 rpm with an Eppendorf Centrifuge, and 240 $\mu$l of the supernatant was applied to a reversed-phase C18 HPLC column (100×250 mm, 5 $\mu$m bead size, 100 Å pore size, prepacked NGA column from The NEST Group). HPLC was performed using an acetonitrile gradient of 0 to 30% in 0.1% TFA in 105 min. at a flow rate of 4.0 ml/min. The elution was monitored by absorbance at 214 nm and 254 nm, and the fractions were collected manually according to the elution profile. Samples representing 5% of each fraction (corresponding to 2 $\mu$l crude venom per sample) were dried by Speed Vac (Savant), suspended in a buffer, and tested for their ability to block $^{45}Ca^{+2}$ influx into rat GH4C1 cells (see "Microscreen Assay for L-Type Calcium Channel Blockers" below). The third major fraction, eluted at an acetonitrile concentration of about 7% (see FIG. 1), inhibited the influx by greater than 80%; it was designated the "DOC" fraction.

(b) Further Fractionation of the DOC Fraction

Figure 2:
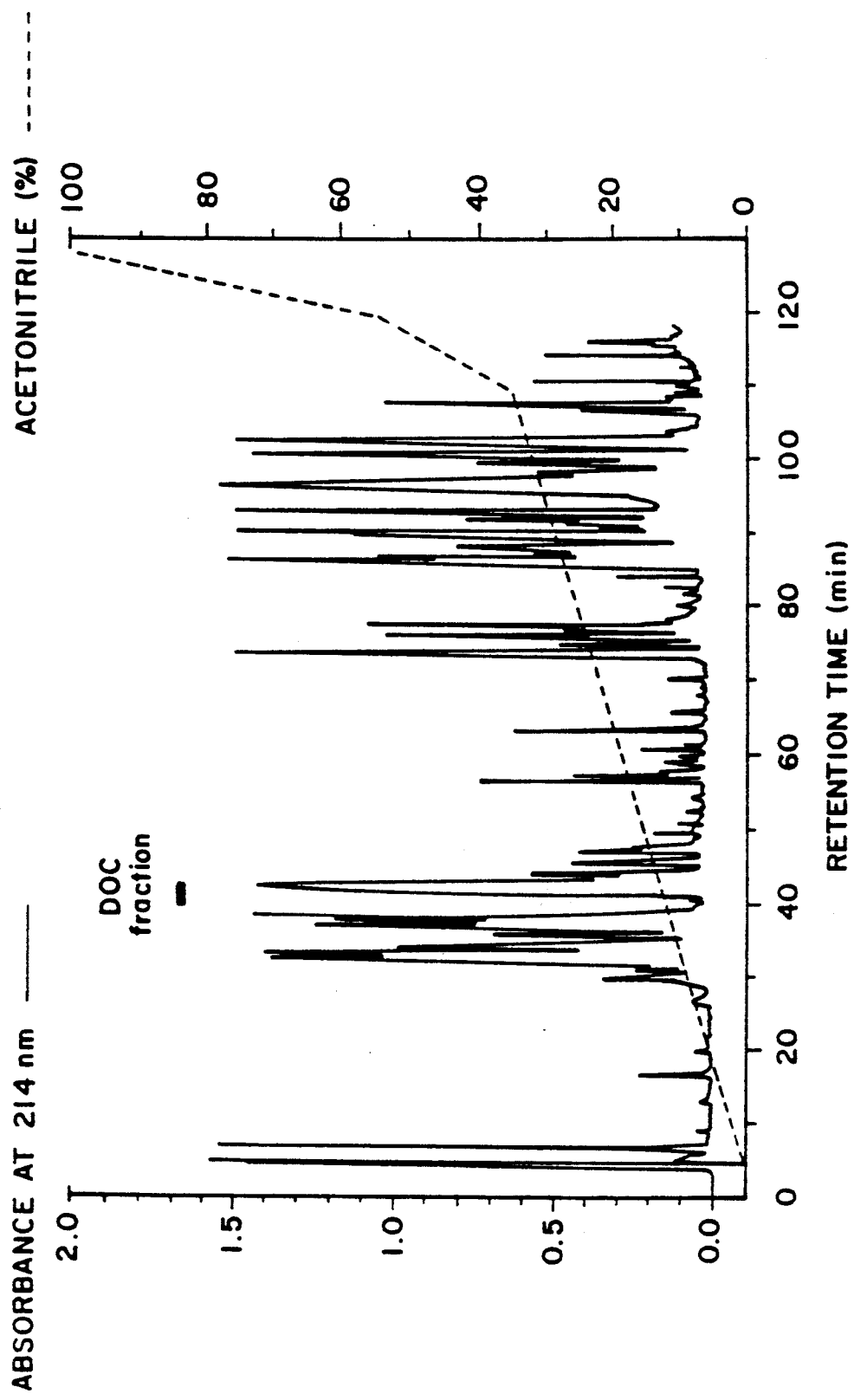
Figure 3:
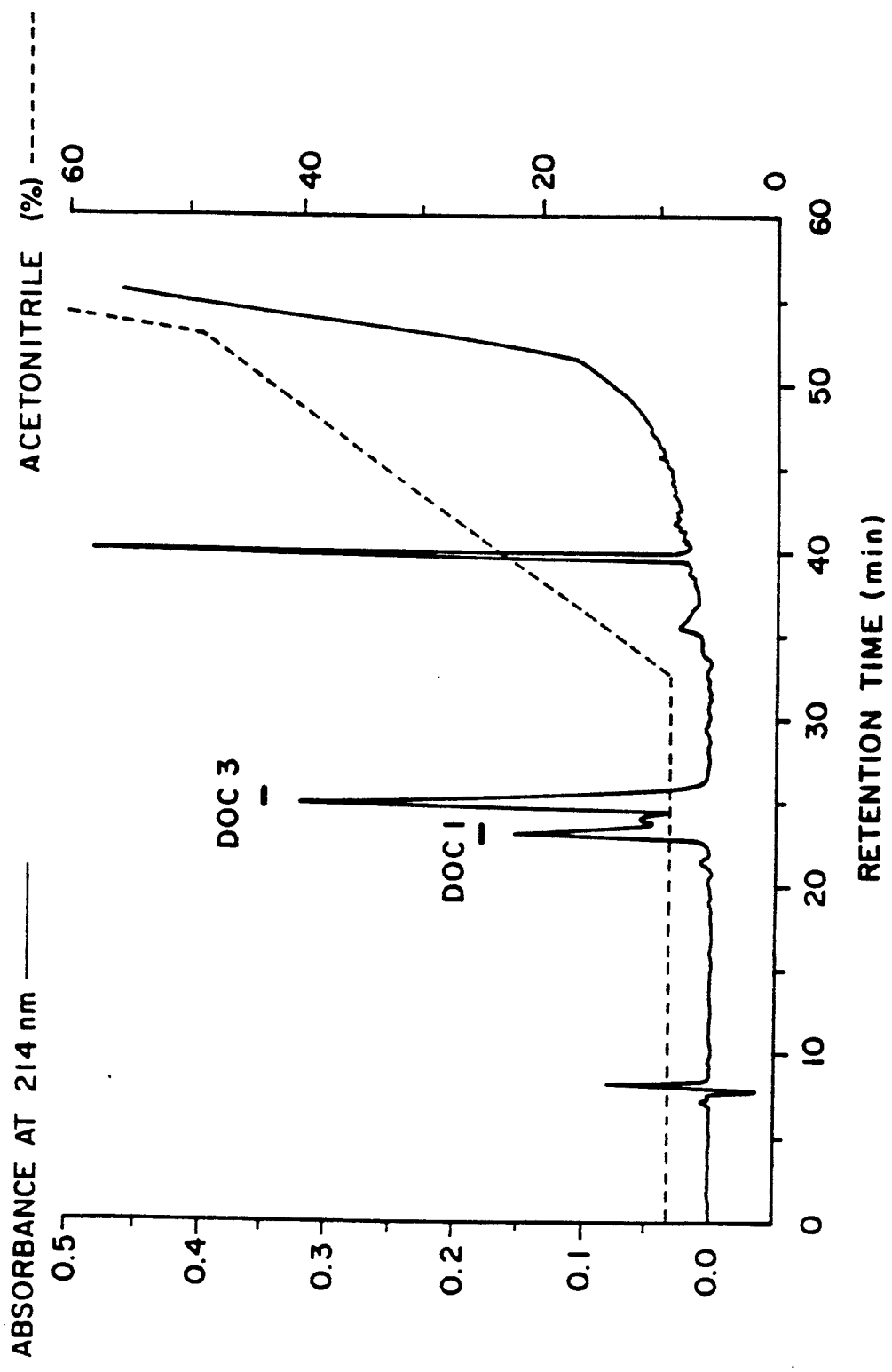

80 $\mu$l of crude venom were mixed with 160 $\mu$l 0.1% TFA, and then fractionated by HPLC as described above. The fraction which eluted at the DOC position (see FIG. 2) was divided into aliquots, dried down with a Speed Vac (Savant), and then dissolved in 0.1% TFA (equivalent to 64 $\mu$l crude venom in 200 $\mu$l 0.1% TFA) for further purification procedures. A 50 $\mu$l portion was applied to a C18 reversed phase HPLC column (100×250 mm, 5 $\mu$m bead size, 100 Å pore size) equilibrated with 9% methanol in 0.1% TFA. The elution was performed at a flow rate of 2 ml/min under isocratic conditions at 9% methanol-0.1% TFA, and monitored by absorbance at 214 nm and 254 nm. The peak fractions were collected manually and dried down with a Speed Vac. The purification procedure was repeated to process all DOC fractions (see FIG. 3).

The first major peak, DOC1, and the second major peak, DOC3, were found to be chromatographically substantially pure, and active in the $^{45}Ca^{2+}$ influx assay. These preparations were used as standards against which subsequent DOC1 and DOC3 preparation were compared.

(c) Further Preparation of DOC1 and DOC3 for Preliminary Structural Analysis DOC1 and DOC3 were prepared as described above, except that two serially connected semi-preparative C18 columns (100×250 mm, 10 $\mu$m bead size, 100 Å pore size, prepacked NGA column from The Nest Group) were used for the second fractionation step, at a flow rate of 2 ml/min with 12% acetonitrile in 0.1% TFA. An elution pattern was obtained which was essentially the same as with the methanol-0.1% TFA solvent system used above. The fractions corresponding to DOC1, the first major peak, and DOC3, the second major peak, were dried down with a Speed Vac and submitted for a preliminary structural characterization after purity was confirmed by HPLC. All other methods were the same as described above.

The identities of these putative DOC1 and DOC3 compounds were confirmed by co-injection with the DOC1 and DOC3 standards, respectively, using an analytical C18 HPLC column. In some cases, the activity of purified fractions was re-confirmed.

(2) Routine Large-Scale Purification Protocol

Figure 4:
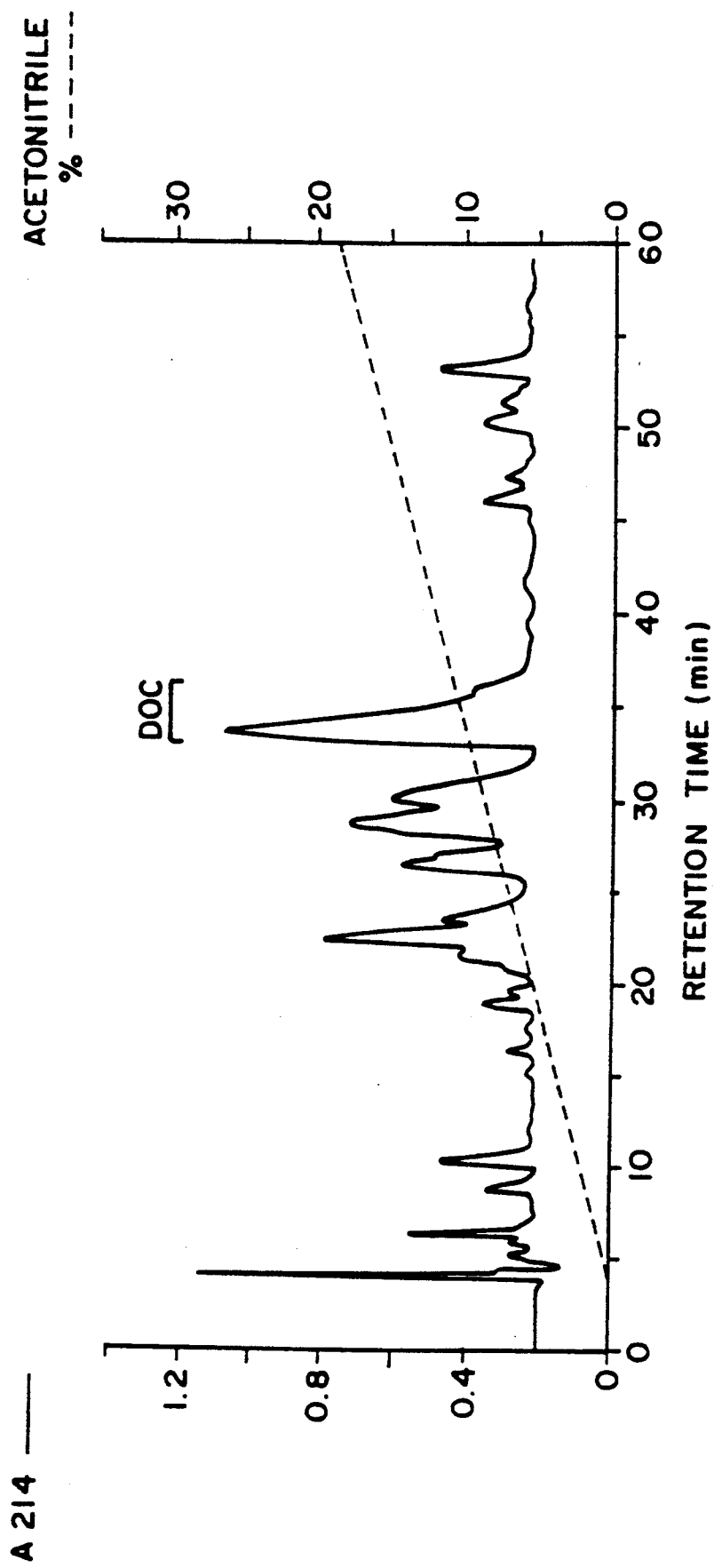
Figure 5:
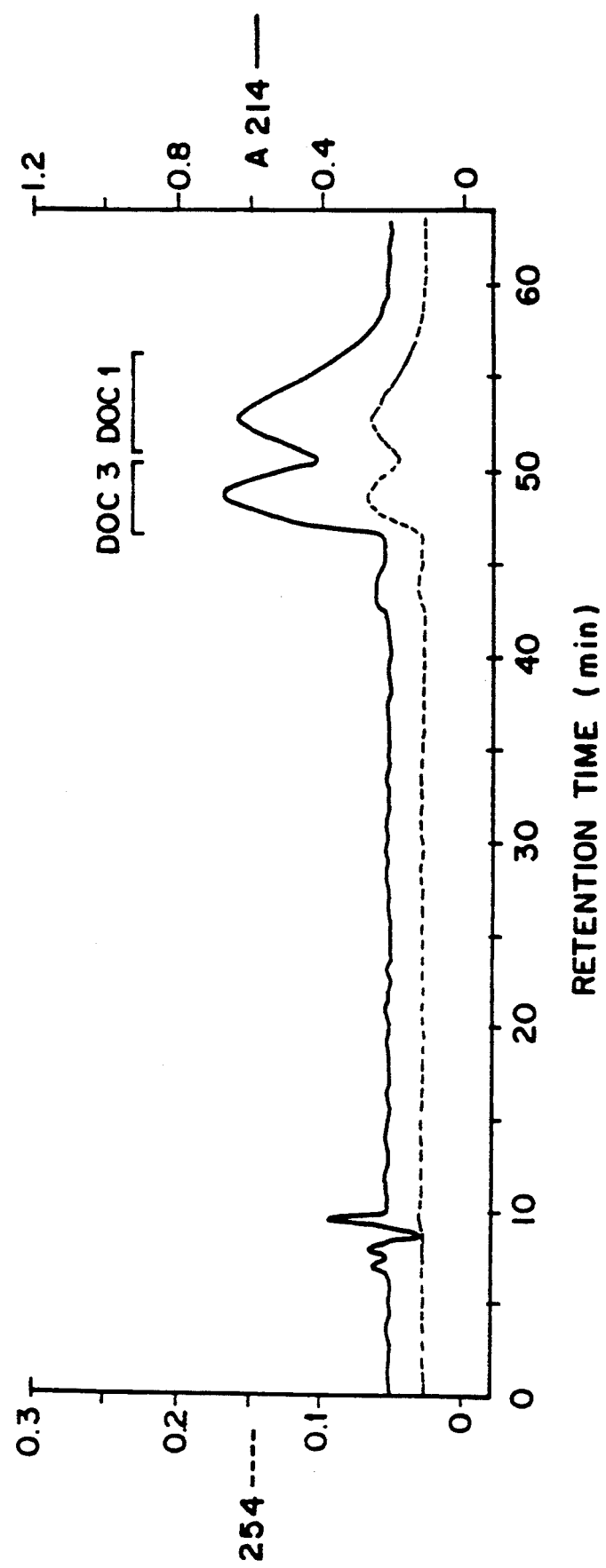

Frozen crude venom (300–400 $\mu$l) was thawed on ice and mixed with 100 $\mu$l of 0.1% TFA. The solution was centrifuged in a cold room for 5 min at 13,000 rpm with an Beckman Microfuge. The supernatant was applied to a reversed-phase C18 HPLC column (200×250 mm, 10 $\mu$m bead size, 100 Å pore size, prepacked NGA column from The Nest Group), and HPLC was performed using an acetonitrile gradient of 0 to 35% in 0.1% TFA, at a flow rate of 16 ml/min for 105 min. The elution was monitored by absorbance at 214 nm, and the fractions were collected manually according to the elution profile. As shown in FIG. 4, the third major peak which was eluted with acetonitrile at a concentration around 10% was designated the DOC fraction and dried with Speed Vac overnight. The dried fraction was dissolved in 200 µl of 0.1% TFA and applied to an ODS-AQ HPLC column (200×250 mm, 10 µm bead size, 100 Å pore size, prepacked YMC column from YMC, Inc.) equilibrated with 10% acetonitrile in 0.1% TFA. The elution was performed with the same buffer at a flow rate of 8 ml/min, and monitored by absorbance at 214 nm (FIG. 5) and 254 nm. The first major peak, which elutes at about 46–50 min of isocratic elution, was collected in several fractions as DOC3. The second major peak, which eluted at about 50–58 min, was collected in several fractions as DOC1. (The order of elution of DOC 1 and DOC3 is reversed when an ODS-AW column was substituted for the ODS-AQ column.) The purity of each fraction was examined by analytical HPLC using a C18 column (4.6×250 mm, 5 µm bead size, 100 Å pore size). Isocratic elution with 9% acetonitrile in 0.1% TFA, followed by a gradient of acetonitrile from 10 to 20% in 5 min. was used at a flow rate of 1 ml/min. The pure fractions (purity greater than 95%) were combined as DOC1 or as DOC3, while those fractions containing a small amount of contamination (less than 20% usually) were combined and repurified further by the same method.

The identity of thus prepared DOC3 was confirmed by the co-injection of a portion of the putative DOC3 sample and the standard DOC3 on a C18 analytical HPLC column (4.6×250 mm, 5 µm bead size, 100 Å pore size). Isocratic elution with 9% acetonitrile in 0.1% TFA, followed by increasing the concentration of acetonitrile to 20% in 5 min was used at a flow rate of 1 ml/min. The absorption spectra (190–390 nm) taken with an on-line diode array detector and the NMR spectra taken with 300 MHz equipment were also used to confirm the identity of the preparation. Typically, about 0.4 mg-1 mg of each of DOC1 and DOC3 was obtained by this procedure from 400 µl crude venom.

Microscreen Assay for L-Type Calcium Channel Blockers

The DOC fraction and DOC1 and DOC3 further purified therefrom were found to possess calcium blocking activity by the following screening method.

(1) SOLUTIONS

All buffers were made up in deionized distilled water (ddH$_2$O). All glassware was rinsed with the same before use.

(a) Hanks Balanced Salt Solution (Hanks)

Purchased from Flow Laboratories (Cat. No. 18-104-49). It was calcium- and magnesium-free and contained phenol red indicator.

(b) 0.02% EDTA Hanks

It was prepared by adding 20 mg EDTA disodium to 100 ml Hanks.

(c) CMT-Hanks

It was prepared from Hanks and contained 16.6 mM CaCl$_2$, 16.3 mM MgCl$_2$, 6.6 mM tris base. The tris base was needed to neutralize the pH change due to the presence of calcium.

(d) Hepes Buffered Basal Salts (HBBS)

It contained 10 mM glucose, 5 mM potassium chloride, 130 mM sodium chloride, 0.5 mM calcium chloride, 1 mM magnesium chloride, and 10 mM hepes; and the pH was adjusted to 7.2 with 40% trisbase.

(e) High Potassium HBBS (KHBBS)

It was the same as HBBS except that 135 mM potassium chloride was substituted for the above sodium and potassium concentrations.

(2) ISOTOPE CALCIUM STOCKS

New England Nuclear $^{45}$Ca stock solution, 24 Ci/g Ca, 50 mCi/ml, was used to prepare high K+ stock and low K+ stock as follows.
  (a) High K+ stock, prepared by adding 10 µl NEN $^{45}$Ca stock to 1 ml HBBS.
  (b) Low K+ stock, prepared by adding 10 µl NEN $^{45}$Ca stock to 1 ml HBBS.

Since there can be substantial error in pipetting these small volumes, 2 µl of each was counted 2× in 10 ml liquid scintillation fluid and the counts were then corrected by adding more volume if there was a difference in total counts greater than 5%.

(3) CELL PREPARATION

The rat GH$_4$C$_1$ pituitary cells, a widely available cell line obtained from Dr. Armen Tashjian, Harvard Medical School, was used to measure effect of DOC preparations on calcium influx into cells. This cell line is well known to have L-type (dihydropyridine sensitive) calcium channels [Tan, K. et al (1984) J. Biol. Chem. 259:418].

Cell stocks were kept frozen in liquid nitrogen until needed. One ampule was thawed and then seeded onto a T-75 culture flask and grown to confluency. Thereafter, the cells were treated with a 1% trypsin solution in Hanks and replated onto T-25 culture flasks at different dilutions. Stocks were then kept growing and split as needed rather than refrozen. The medium used was Ham's F-10 supplied by Media-Tech containing 10% heat-inactivated fetal calf serum purchased from Hyclone. In general, the best response was obtained from 3–5 day post-confluent cells.

Cell suspension from one T-25 flask was prepared as follows for experiments. The flask was gently washed 2× with Hanks. 10 ml of warm 0.02% EDTA-Hanks was added to the flask and allowed to stand for approximately 30 seconds. The plate was sloshed, inverted and banged on a hard surface to dislodge the cells. 0.6 ml CMT-Hanks was immediately added and sloshed. The cells were then transferred to a 15 ml centrifuge tube and spun for 20–30 seconds at 50 g (700 RPM).

With a pipette, the supernatant was gently aspirated and resuspended by triturating the pellet in 0.4 ml HBBS. The cells were then transferred to a 4 ml flat bottom glass vial with a magnetic flea and stirred at the slowest speed.

(4) ASSAY PROCEDURE

A dried venom preparation, e.g., DOC1 or DOC3, was suspended in 7 µl HBBS and 1 µl thereof was added to 3.2 µl cell suspension in a 1 ml microfuge tube and pre-incubated for 5 min. Thereafter, low K+ or high K+4.2 µl $^{45}$Ca stock [eq. to 2 uCi/4.2 µl cells] was added to the tube and incubation was continued for 1 min. 790 µl HBBS was added to quench calcium uptake by the cells. The mixture was then pipetted up and down 2× before it was subjected to filtration in an Amicon filter manifold with a Whatman glass fiber filter. The filter was rinsed 5× with 5 ml HBBS buffer each. It is important that the buffer be squirted at the side of the chimney, straight down and not directly at the filter, since this may wash cells back up off the filter and onto the chimney. It is also important not to cause a whirlpool effect with the wash and create uneven rinsing of the filter.

A separate chimney for each well was used and each chimney was washed after use. Also, the filter was rinsed once just before transferring cells onto it so that it was moist and did not cause cells to rupture upon contact therewith.

About 1 min. after the rinse, the chimney was removed to relieve the filter of suction to minimize loss of counts due to cell disruption. A set of four blanks (i.e., measurements using the same solutions but without cells) was run at the end of the assay to determine the background counts.

The filter was then shaken and dissolved in 10 ml liquid scintillation fluid (hydrofluor) and counted for 5 min. using a beta scintillation counter. Calcium uptake induced by $K^+$, i.e., depolarization, was determined from the high $K^+$ samples after substraction of the averaged blank counts and corresponding low $K^+$ counts. Note that the cells were depolarized by an elevated $K^+$ concentration in order to open the voltage-activated calcium channels.

The percentage of calcium uptake blocked by a given venom preparation was calculated based on the levels of the $Ca^{+2}$ uptake induced by $K^+$ in the presence and absence of the preparation.

Cell concentration was also determined using a hemocytometer so that uptake/mg protein could be calculated.

(5) RESULTS

Figure 6:
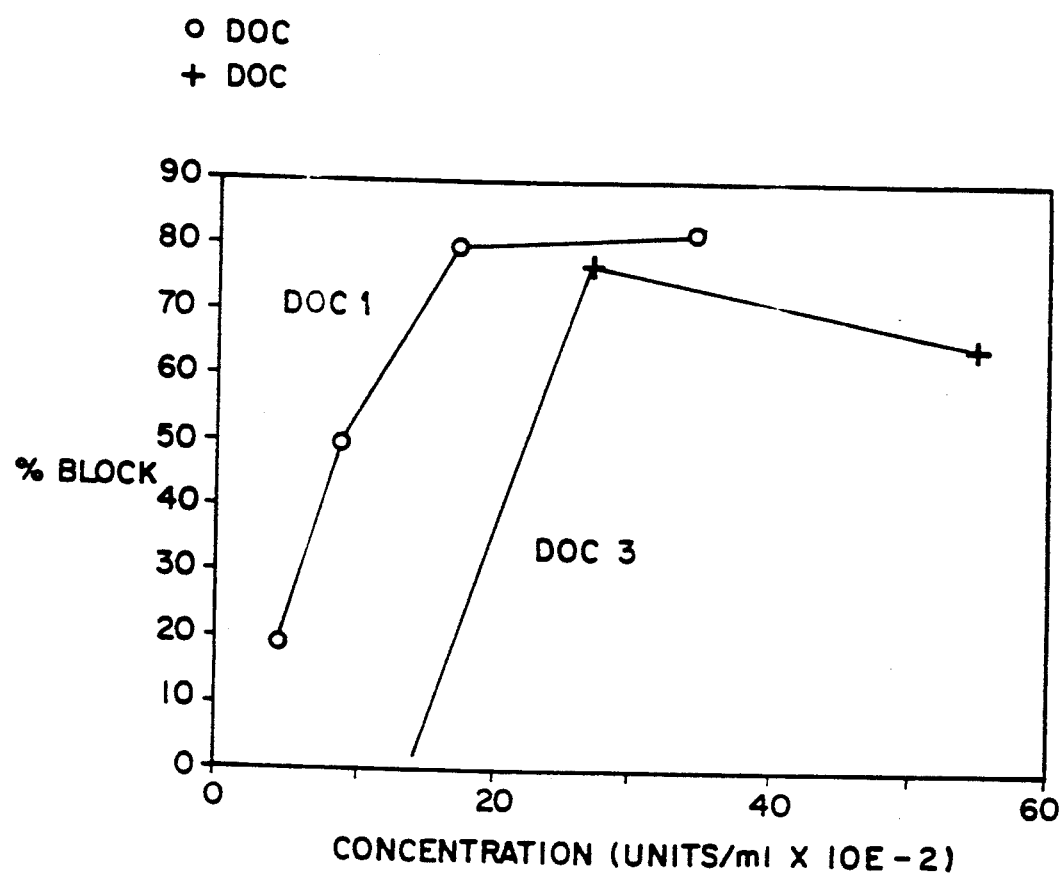
FIG. 6 is a graph showing that DOC1 and DOC3, two compounds purified from spider venom, each blocked potassium-stimulated calcium uptake by $GH_4C_1$ clonal pituitary cells.

FIG. 6 shows the blocking activities of DOC1 and DOC3, respectively, in this assay. DOC1 is several-fold more potent than DOC3. As will be shown below, the blocking activity of DOC1 was confirmed by electrophysiological experiments. Note that 1 unit of DOC1 or DOC3 is defined as absorbance of 1 0.D. at 214 nm in 1 ml of aqueous solution.

Structural Elucidation of DOC1 and DOC3

The UV spectra of DOC1 and DOC3 both show a pattern characteristic of a 4-hydroxyindole. In addition, DOC1 and DOC3 both have four proton signals in their $^1$H-NMR spectra between 6.4 and 7.1 ppm, which is consistent with a 4-hydroxyindole with substitution at the 3 position. The singlet (2H) at 3.65 ppm indicates that there is an acetic acid unit at the 3 position (rather than a lactate). Therefore, both DOC1 and DOC3 contain 4-hydroxyindole-3-acetic acid units.

Two dimensional double quantum filtered correlation spectroscopy (DQ-COSY) of DOC3 shows the presence of a five methylene unit ($NCH_2CH_2CH_2CH_2CH_2N$) and three methylene units ($NCH_2CH_2CH_2N$).

The difference between the $^1$H-NMR of DOC1 and DOC3 seems to be the presence of three additional methylene signals in DOC1. Two of these signals are at 2.8-3.1 ppm, which means that they are adjacent to nitrogen. The other methylene signal is around 18 ppm which is appropriate for the central methylene in a three methylene unit.

The fast-atom bombardment (FAB) mass spectrometry of DOC1 reveals a molecular weight of 446. Therefore, DOC1 contains a 4-hydroxyindole-3-acetic acid, a 5-methylene unit and three 3-methylene units.

The tentative structure assigned to DOC1 is shown in formula II above. DOC3 is believed to be of very similar structure to DOC1, but appears to have a shorter polyamine chain.

Synthetic Methods for DOC1, DOC3 and Their Analogs

The synthesis of DOC1, DOC3 and their related analogs can be best achieved in three steps, namely, synthesis of a polyamine unit with desired substituents on it, synthesis of a suitably substituted 3-indole acetic acid unit, and condensation of polyamine and indole units. This strategy has been used for the synthesis of polyamine-containing compounds of various types. [Bruce, M. et al. (1990) Toxicon 28:1333].

(1) Synthesis of Polyamine

Figure 7:
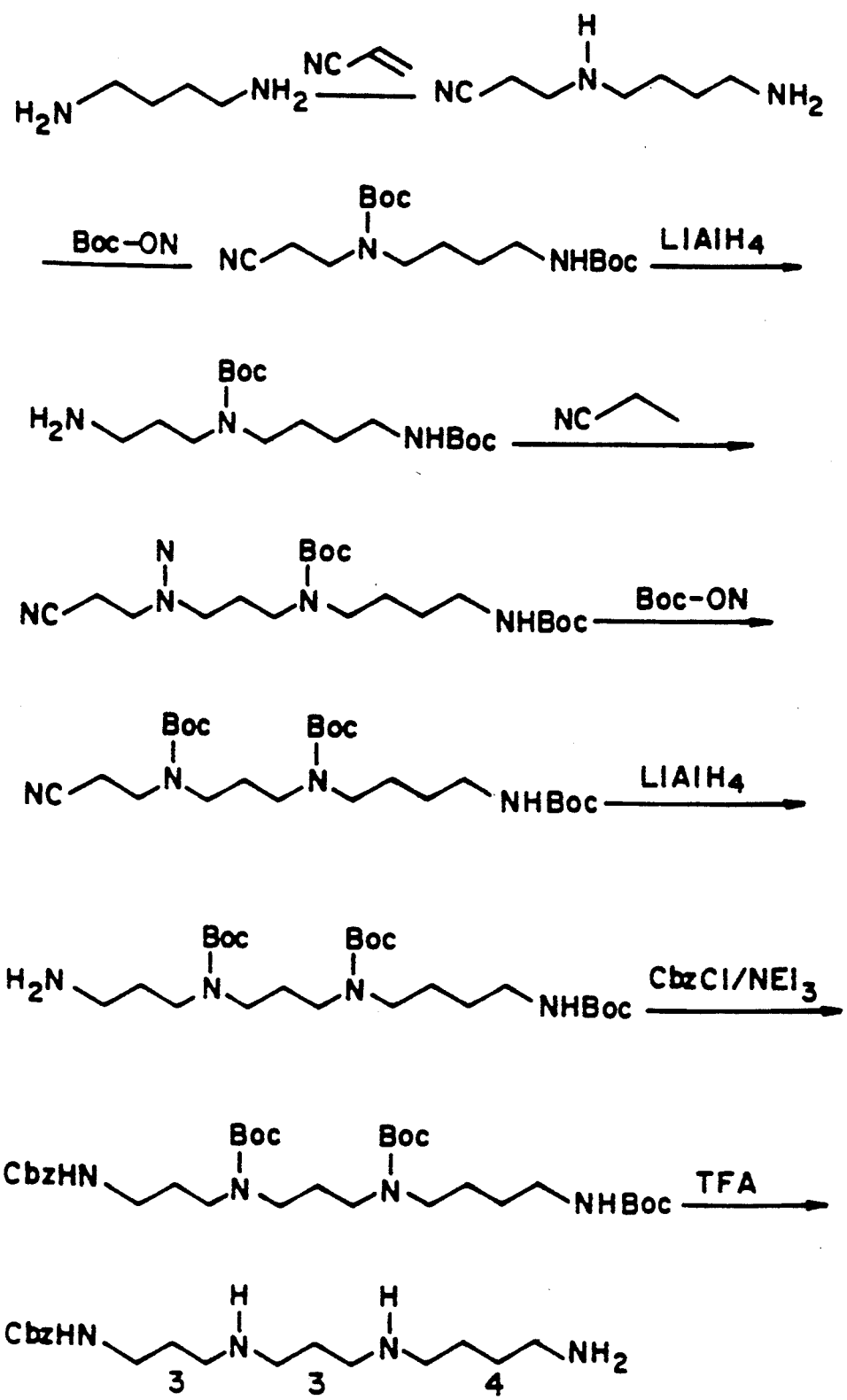
FIGS. 7-9 are synthetic schemes for synthesizing DOC1, DOC3, and their analogs.

Extensive methodology has been developed for the synthesis of polyamines in recent years. [Saccomano, N. A. et al. (1989) Ann. Rep. Med. Chem. 24:287; Ganem, B. (1982) Acc. Chem. Res. 15:290; and Carboni, B. (1988) Tetrahedron Lett. 29:1279]. Since many types of diaminoalkanes (e.g. $C_2$-$C_{12}$ chain) are commercially available, e.g., see Aldrich Chemical Catalog 1990/1991, and the methods for assembling different diamine units are well known in the literature, it is possible to synthesize polyamines containing virtually any combination of alkane units. In a typical example of 3,3,4-polyamine synthesis, the synthesis starts from 1,4-diaminobutane as depicted in Scheme I of FIG. 7 [Nakanishi, K. et al. (1990) Pure & Appl. Chem. 62:1223], and uses the following standard organic reactions:

(a) Michael addition of amine to an acrylonitrile. This reaction was originally developed by Shih, T. L. et al. (1987) Tetrahedron Lett. 28:6015, and later used by Jasys V. J. et al. (1990) J Am. Chem. Soc. 112:6696 for synthesizing various polyamine units.

(b) Boc-protection reaction, an excellent yielding step. Boc protection is commonly used to protect nitrogens, particularly in synthetic peptide chemistry.

(c) Reduction of nitrile to an amine was effected by using one of the following reagents, depending on the type of protecting groups used in the polyamine synthesis: (i) LiAlH$_4$, [Nakanishi, K. et al. (1990) Pure & Appl. Chem. 62:1223]; (ii) Pearlman catalyst Pd(OH)$_2$, HOAc, [Jasys V. J. et al. (1990) J. Am. Chem. Soc. 112:6696]; (iii) Raney Ni, [Shih, T. L. et al. (1987) Tetrahedron Lett. 28:6015]. The yields of the above reactions are very good, thus enabling one conveniently to synthesize large amounts of the polyamines.

Using the above synthetic strategy (Scheme I, FIG. 7), it is possible to synthesize substituted polyamine units as well:

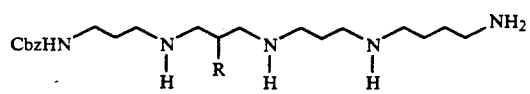

-continued
R = CH₃, C₂H₅, C₃H₇, C₄H₉ etc.

The synthesis uses a substituted diaminoalkane (R=alkyl) as starting material. The reaction of diamine with acrylonitrile followed by the standard organic reactions described in Scheme I (FIG. 7) should yield the requisite polyamine. For synthesis of a straight chain α, ω-diaminoalkane unit, diamines having up to C₁₂ carbon units are commercially available. E.g., see Aldrich Chemical Catalog 1990/1991.

The terminal amino group of a polyamine unit may be replaced with a guanidine or N-substituted guanidine moiety. Once the desired unit of polyamine has been prepared by using the method in Scheme I (FIG. 7), the free amino group on the unit can be reacted with an N-substituted cyanamide to give the desired guanidine. Reaction of amine with substituted cyanamide to yield guanidine is a well established method. [Scherz, M. W. et al. (1990), J. Med. Chem. 33:2421].

(2) Synthesis of Substituted Indole-3-Aliphatic Acid

Figure 8:
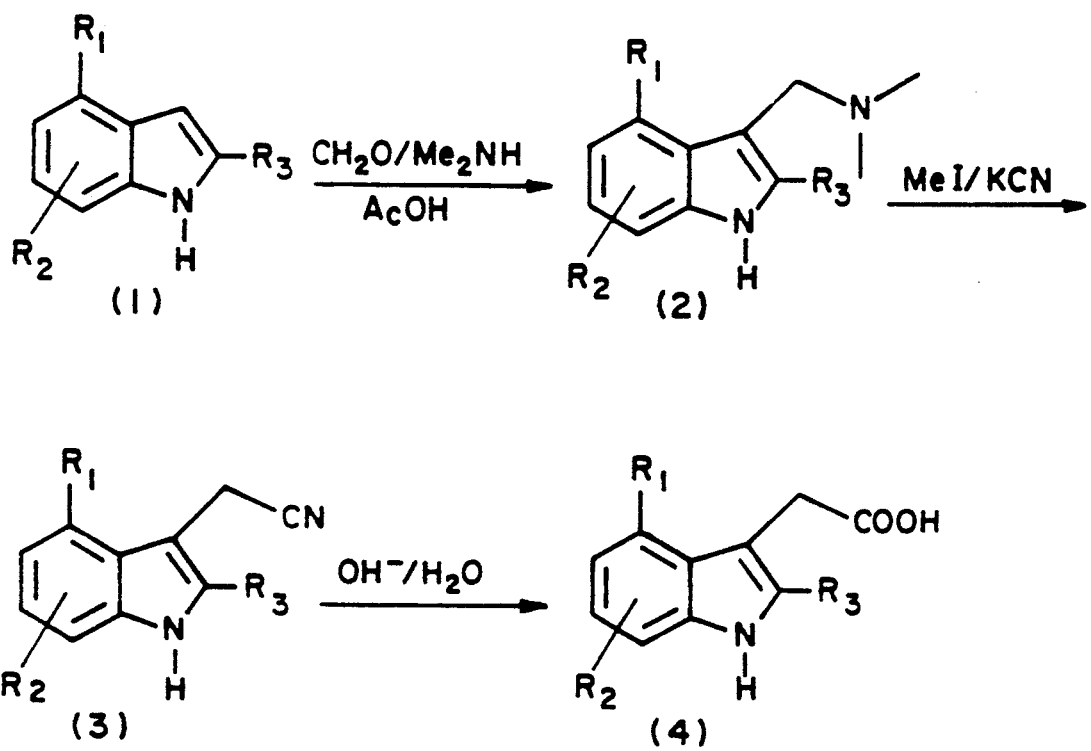

The general procedure of preparing mono-, di-, and tri-substituted indole-3-acetic acids starting from the corresponding indoles are shown in Scheme II (FIG. 8). The commercially available mono-substituted or di-substituted indoles (e.g. 4-methoxyindole, 5-methoxyindole, 5,6-dimethoxyindole, 5-benzyloxyindole, 4-hydroxyindole, 5-hydroxyindole, 5-bromoindole, 5-bromo-7-nitroindole, 4-chloroindole, 5-chloroindole, 6-chloroindole, 5-chloro-2-methylindole, 5-fluoroindole, 5-aminoindole, 4-nitroindole, 5-nitroindole, indole-4-carboxylic acid, indole-5-carboxylic acid, 2,5-dimethylindole, 1-methylindole, 3-methylindole, 4-methylindole, 5-methylindole, 6-methylindole) can be used as starting materials in the synthesis of indole-3-acetic acids (Scheme II, FIG. 8), either directly or with slight modifications. The above substituted indoles are available, for example, from Aldrich Chemical Co.

In those cases where the existing functional group is sensitive to the reaction conditions, it would be protected first. The substituted indole (compound 1 in Scheme II, FIG. 8) is first converted to substituted-gramine (compound 2 in Scheme II, FIG. 8) by a mannich reaction following the procedures of Stoll, A. et al. (1955) Helv. Chem. Acta 38:1452 and Poon, G. et al. (1986), J. of Labelled Compounds and Radiopharmaceuticals 23:167. The dimethylamine portion in compound 2 is then displaced by cyanide to form substituted-indole-3-acetonitrile (compound 3 in Scheme II, FIG. 8) by refluxing with potassium cyanide in ethanol/water. [Poon, G. et al. (1986), J. of Labelled Compounds and Radiopharmaceuticals 23:167]. Finally, the desired substituted indole-3-acetic acid (compound 4 in Scheme II, FIG. 8) is obtained by acid hydrolysis or base hydrolysis of compound 3 [Poon, G. et al. (1986), J. of Labelled Compounds and Radiopharmaceuticals 23:167].

Figure 9:
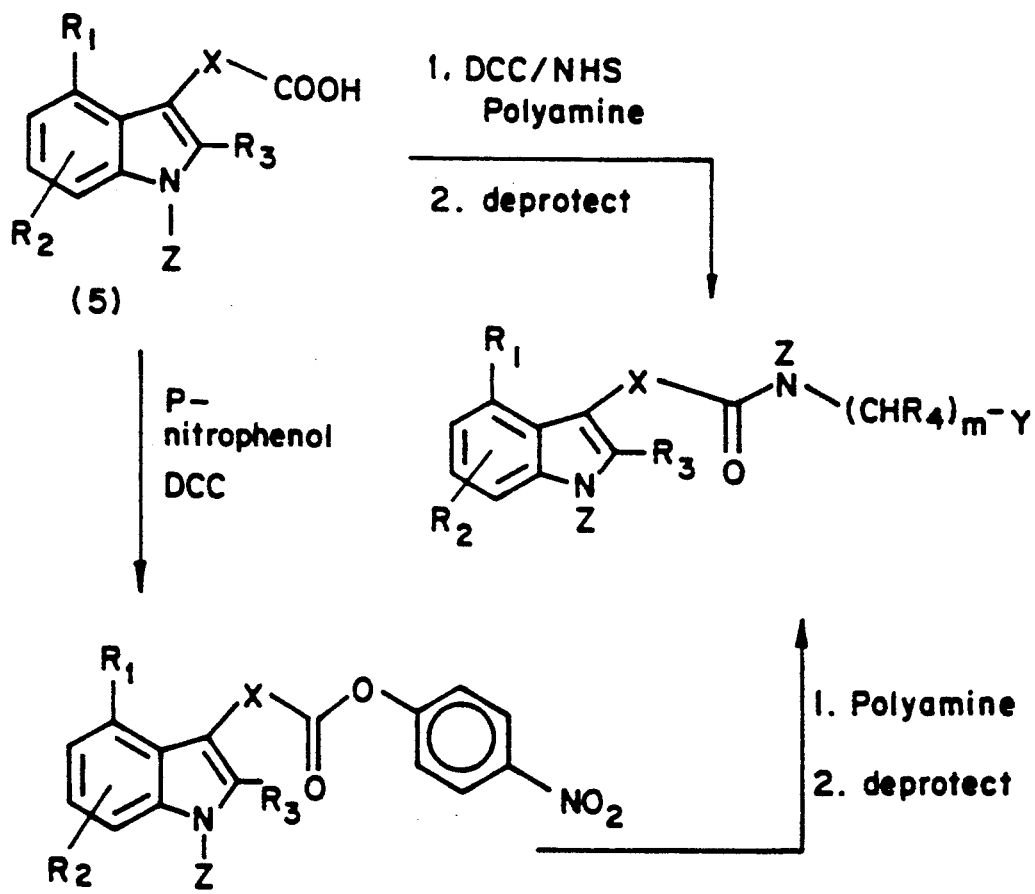

The above procedures are not essential in the following cases: 3-acetylindole, 3-indoleacrylic acid, 3-indolepropionic acid, 3-indolebutyric acid, 2-methyl-3-indoleacetic acid since these compounds are commercially available. They can be applied in the coupling step (Scheme III, FIG. 9) once the required indole units, i.e., compound 5 in Scheme III, are available.

(3) Condensation of Polyamine with Indole Unit

The coupling of substituted indole (compound 5 in Scheme III, FIG. 9) with a t-Boc or Cbz protected polyamine is achieved in the presence of dicyclohexylcarbodiimide/N-hydroxysuccinimide as described by Jasys V. J. et al. (1990) J. Am. Chem. Soc. 112:6696, or by using the p-nitrophenol activated ester of compound 5 and polyamine as described by Nakanishi, K. et al. (1990) Pure & Appl. Chem. 62:1223. (Scheme III, FIG. 9). Finally, deprotection will give DOC1 or an analog thereof [Nakanishi, K. et al. (1990) Pure & Appl. Chem. 62:1223]. (Scheme III, FIG. 9).

The acetyl benzoyl, phenacetyl, benzyloxy carbonyl and various alkoxycarbonyl derivatives of DOC1 or its analogs can be made to increase the lipophilicity of the compound, and thus its ability to cross the blood-brain barrier [see, e.g., "Design of Prodrugs", published by Elsevier (1985) edited by Bundgaard, pp. 27–35]. These derivatives act as prodrugs, and the methods to prepare these prodrugs are well documented in the literature [Dittert, L. W. et al. (1968) J. Pharm. Sci. 57:828; Inoue, M. et al. (1979), J. Pharm. Dyn. 2:229; and Dittert, L. W. et al. (1968) J. Pharm. Sci. 57:774].

(4) Derivatization of DOC1, DOC3 and their Analogs

Acetates: The most commonly used method for preparing these derivatives of a primary or secondary amine is treating the amine with acetic anhydride as described in Vogel's textbook of Practical Organic Chemistry, Fourth Edition, pp. 1128. Benzoates and Phenacetates: These derivatives of a primary or secondary amine are best made by treating the amine with corresponding benzoyl chloride or phenacetyl chloride as described in Schotten-Baumann Reaction, in Vogel's Text Book of Practical Organic Chemistry, Fourth Edition, pp. 682. Carbamates: The synthesis of carbamates of a primary or secondary amine is best achieved by treating the amine with CO, O₂, and R—OH in the presence of Pt and iodide ion according to Fukuoka et al. (1984) J. Org. Chem., 49:1458. This method can produce alkoxycarbonyl or benzyloxycarbonyl derivatives, depending on the type of alcohol used in the reaction. Specifically, the aliphatic alcohols give the alkoxycarbonyl derivative, whereas the aromatic alcohols produce the aryloxycarbonyl type of derivatives.

Microscreen Assay for Blockers of Synaptosomal Calcium Channels

The screening method used to test calcium blocking activity in GH₄C₁ cells of venom preparations, as described above, was modified as follows for determining the effect of DOC1 on synaptosomal calcium uptake.

| (1) BUFFERS (in mM) | | | | |
| --- | --- | --- | --- | --- |
|  | Low K | Low K + Ca | High K + Ca | Quench |
| HEPES | 10 | 10 | 10 | 10 |
| D-Glucose | 10 | 10 | 10 | 10 |
| KCl | 3 | 3 | 150 | 3 |
| NaCl | 147 | 147 | 0 | 147 |
| MgCl₂ | 1.2 | 1.2 | 1.2 | 1.2 |
| CaCl₂ | 0 | 3.3 | 3.3 | 0 |
| Tris-EGTA | 0 | 0 | 0 | 10 |

After the buffers were made, the osmolarity of the quench buffer was adjusted by dilution with ddH₂O to approximately equal to the average of the osmolarities of the other 3 buffers. All the buffers were made up in ddH²O only.

(2) CALCIUM 45 STOCKS

For basal uptake: 5 µl NEN stock+995 µl low K+Ca buffer.

For depolarized (i.e., high K+) uptake: 5 µl NEN+995 µl high K+Ca buffer.

(3) SYNAPTOSOME PREPARATION

The synaptosome preparation described below was an adoption of a published procedure. [Hajos F., Brain Res. 93:485–489 (1975)].

Basal buffer used was of the following composition: Basal buffer, pH 7.4, was of following composition: NaCl 147 mM, KCl 3 mM, HEPES 10 mM, Dextrose 10 mM, $MgCl_2$ 1.2 mM, and EGTA-Tris 1 mM. The high-K+ buffer was the same as the basal buffer except that concentrations of NaCl and KCl were 95 mM and 55 mM, respectively.

Synaptosomes were prepared from CD male rats of 4 to 6 weeks (50–75 g). Rats were killed by decapitation with guillotine, and the skull bone was opened in the center with the pointed blade of dissection scissors. The bone was then peeled away with a bone cutter and the brain pried with a micro spatula. Thereafter, the cerebellum was removed and the rest of the brain placed in 35 ml of 0.32M sucrose solution and homogenized in a Thomas glass teflon homogenizer C at maximum power setting (about 450 rpm) with 16 strokes. The pestle was rinsed with 5 ml of sucrose solution and the wash added to the homogenate.

The homogenate was then centrifuged for 10 min. at 3,500 rpm (1,500 g) in an SS-34 rotor in a Sorvall RC-5B centrifuge. The resulting pellet ($P_1$) was discarded and the supernatant ($S_1$) was recentrifuged for 20 min. at 8,700 rpm (8,500 g). The resulting supernatant ($S_2$) was discarded and the pellet ($P_2$) resuspended in 5 ml of 0.32M sucrose and hand-homogenized with 4 strokes in a Thomas C homogenizer. The volume was brought up to 8 ml with a 0.32M sucrose solution.

This homogenate was layered on 20 ml of 0.8M sucrose solution in two centrifuge tubes and spun for 25 min. at 8,700 rpm (8,500 g). At the end of the spin, most of the myelin stayed at the interphase of 0.32M and 0.8M sucrose, the mitochondria formed as a brown pellet at the bottom of the tube, and the synaptosomes was dispersed in 0.8M sucrose. A 10 ml pipette was used to collect the 0.8M sucrose layer without disturbing the top myelin layer or the pellet. The collected solution was diluted slowly with an equal volume of chilled basal buffer, while stirring gently with a Pasteur pipette. This diluted solution was centrifuged for 10 min at 10,000 rpm (12,000 g). The pellet thus formed was resuspended in 1.5 ml of basal buffer and hand-homogenized with 8 strokes in a Wheaton glass-glass 7 ml homogenizer. The suspended synaptosomal preparation was stored frozen at −70° C. until needed.

(4) ASSAY PROCEDURE

The assay procedure is similar to that described above under the heading "Microscreening for L-Type Calcium Channel Blockers".

The synaptosomal preparation was thawed on ice and diluted to 500 µl with ice-cold low K buffer. An 3.2 µl aliquot was warmed at 30° C. for 3 min. just before addition of 1 µl DOC1. After preincubation, 4.2 µl $^{45}Ca^{+2}$ stock, either low K or high K, was added and calcium uptake quenched 5 seconds after the addition with 900 µl quench buffer. The filter was rinsed 3× with 5 ml quench buffer each. The filter was then removed and placed in a scintillation vial containing 10 ml Hydroflour scintillation cocktail and shaken vigorously until it dissolved. A beta-scintillation counter was used to count each vial for 5 min.

Filters used were Millipore HA 0.45 µm #HAWP 025 00 and a Brinkmann Dispensette was used to rinse the filters. The quench buffer was used to pre-wet the filter prior to applying the synaptosomes.

(5) RESULTS

The experimental results (not illustrated) indicate that DOC1 produced some block of K+-stimulated calcium uptake by synaptosomes. However, none of the concentrations tested (up to 0.5 units/ml) inhibited the calcium uptake by more than about 30%. Thus, DOC1 is substantially less effective and potent in blocking synaptosomal calcium channels in comparison with its ability to block L-type calcium channels in $GH_4C_1$ clonal pituitary cells.

Electrophysiological Studies of DOC1

(1) CELL PREPARATION

The activity of DOC1 was examined in electro-physiological experiments on two mammalian cell lines that express different subclasses of calcium channels: the rat clonal pituitary cell line $GH_4C_1$, which expresses L-type calcium channels, and the murine neuroblastoma cell line N1E-115, a widely available cell line (obtained in this instance from Dr. Mark Fishman, Massachusetts General Hospital), which expresses L-, T- and R-type calcium channels [Knapp et al. (1990) Soc. for Neurosci. Abs. 16:678].

$GH_4C_1$ cells were maintained and handled as described above under the heading "Microscreening for L-Type Calcium Channel Blockers". Aliquots of freshly resuspended cells were dispensed into the recording chamber immediately prior to electrophysiological experiments.

N1E-115 cells were grown at 37° C. in Ham's F-12 medium supplemented with 10% fetal calf serum. Stock cultures maintained in polystyrene flasks were fed once a week and split 1:10 once a week. For electrophysiological experiments, cells were split 1:4 or 1:8 and replated on untreated 35 mm polystyrene dishes or on glass coverslips coated with poly-D-lysine (4 µg/ml)+laminin (10 µg/ml). Cells were induced to differentiate by adding 2% dimethylsulfoxide to the culture medium for 7–21 days Quandt, F. N. et al. (1984) Neuroscience 13:249]. This treatment causes N1E-115 cells to assume a neuron-like morphology and to express a high density of voltage-dependent calcium channels.

(2) ELECTROPHYSIOLOGICAL METHODS

Ionic currents through calcium channels were recorded with patch electrodes in the whole-cell voltage-clamp configuration [Hamill, O. et al. (1981) Pflugers Arch. 391:85]. Briefly, cells were placed in an extracellular solution containing (in mM) 130 TEA-Cl, 5 $BaCl_2$, 10 glucose 10 HEPES, 0.5 µM TTX, pH 7.2. The intracellular (pipette) solution contained (in mM) 125 CsCl, 10 EGTA, 10 HEPES, 4 $Mg_2ATP$, pH 7.2.

These solutions were designed to prevent currents through all voltage-dependent ion channels other than calcium channels. $Ba^{+2}$ was used as the charge carrier to prevent calcium-dependent inactivation of calcium channels. Cell membrane potential was controlled electronically. Current through calcium channels was elicited by step depolarizations from negative holding potentials. DOC1 was dissolved in the extracellular solution and applied to cells by pressure ejection from a glass micropipette.

(3) RESULTS

Figure 10:
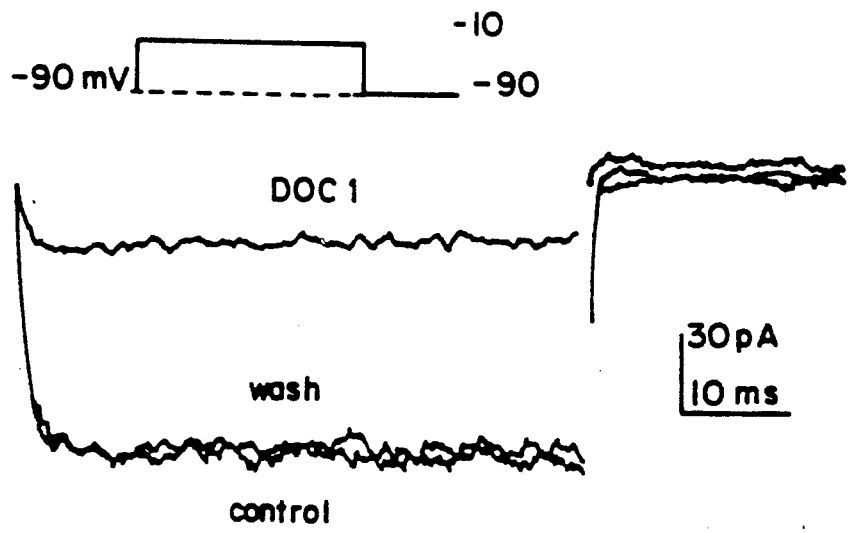
FIG. 10 is a graph showing that DOC1 is capable of reversibly blocking electrical current through calcium channels of $GH_4C_1$ clonal pituitary cells.

In GH$_4$C$_1$ cells, we examined the effect of DOC1 on sustained currents evoked by relatively large depolarizations to between −10 and +20 mV. Under these conditions, current is likely to be primarily through L-type calcium channels (Mattson, D. R. & Armstrong, C. M. *J. Gen Physiol.* 87:161–182, 1986). Consistent with the results of the calcium flux experiments, DOC1 (0.4–1.0 U/ml) reversibly blocked a large fraction (up to 80%) of current through calcium channels (FIG. 10).

The actions of DOC1 on additional classes of calcium channels was examined in N1E-115 cells. In these experiments, L-type channels were blocked by inclusion of 10 μM nimodipine (a saturating concentration) in the extracellular solution. Under these conditions, N1E-115 cells continued to display a transient, low-threshold (T-type) calcium current as well as one or more high-threshold current components not inhibited by dihydropyridine antagonists [Knapp, A. G. et al. Soc. Neurosci. Abstr. (1990) 16:678].

Figure 11A:
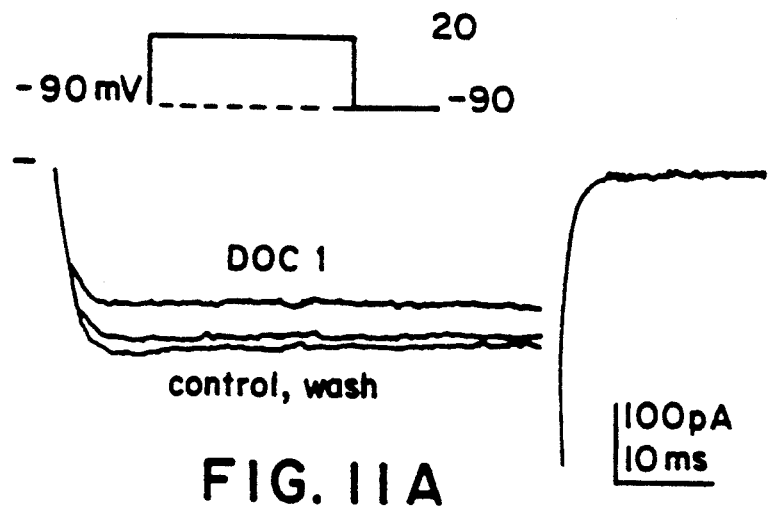
FIGS. 11A and 11B are graphs showing that DOC1 blocks high-threshold current through calcium channels of N1E-115 cells neuroblastoma cells in the presence of nimodipine.
Figure 11B:
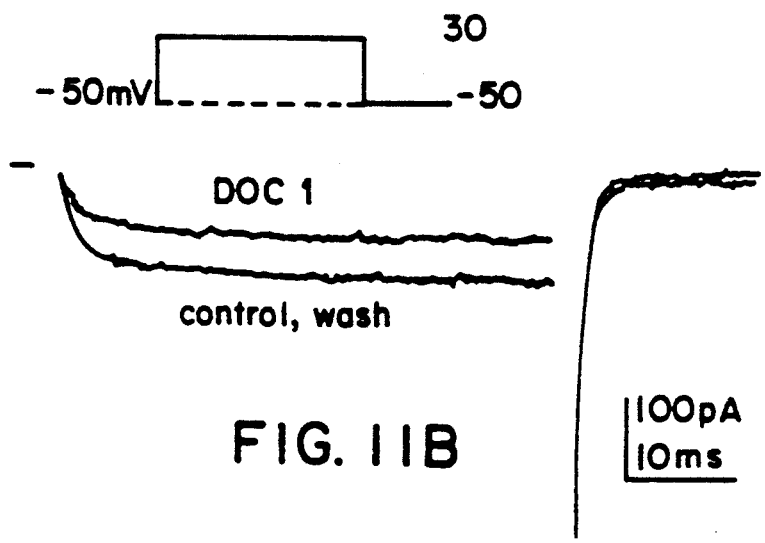
Figure 11C:
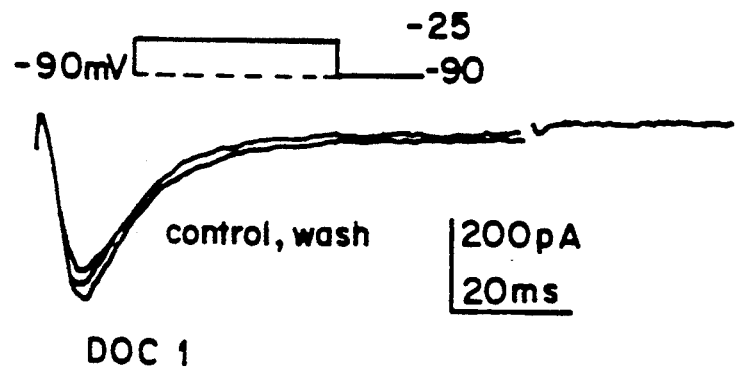
FIG. 11C is a graph showing that DOC1 has little effect on T-type current of N1E-115 cells evoked by weak depolarizations from negative holding potentials.

As shown in FIG. 11A and FIG. 11B, DOC1 (1.0 U/ml) caused inhibition of the high-threshold current through calcium channels even in the continuous presence of nimodipine. DOC1 did not substantially affect the T-type current evoked by weak depolarizations from negative holding potentials (FIG. 11C). The actions of DOC1 were reversible upon washout and were dose-dependent.

Figure 12:
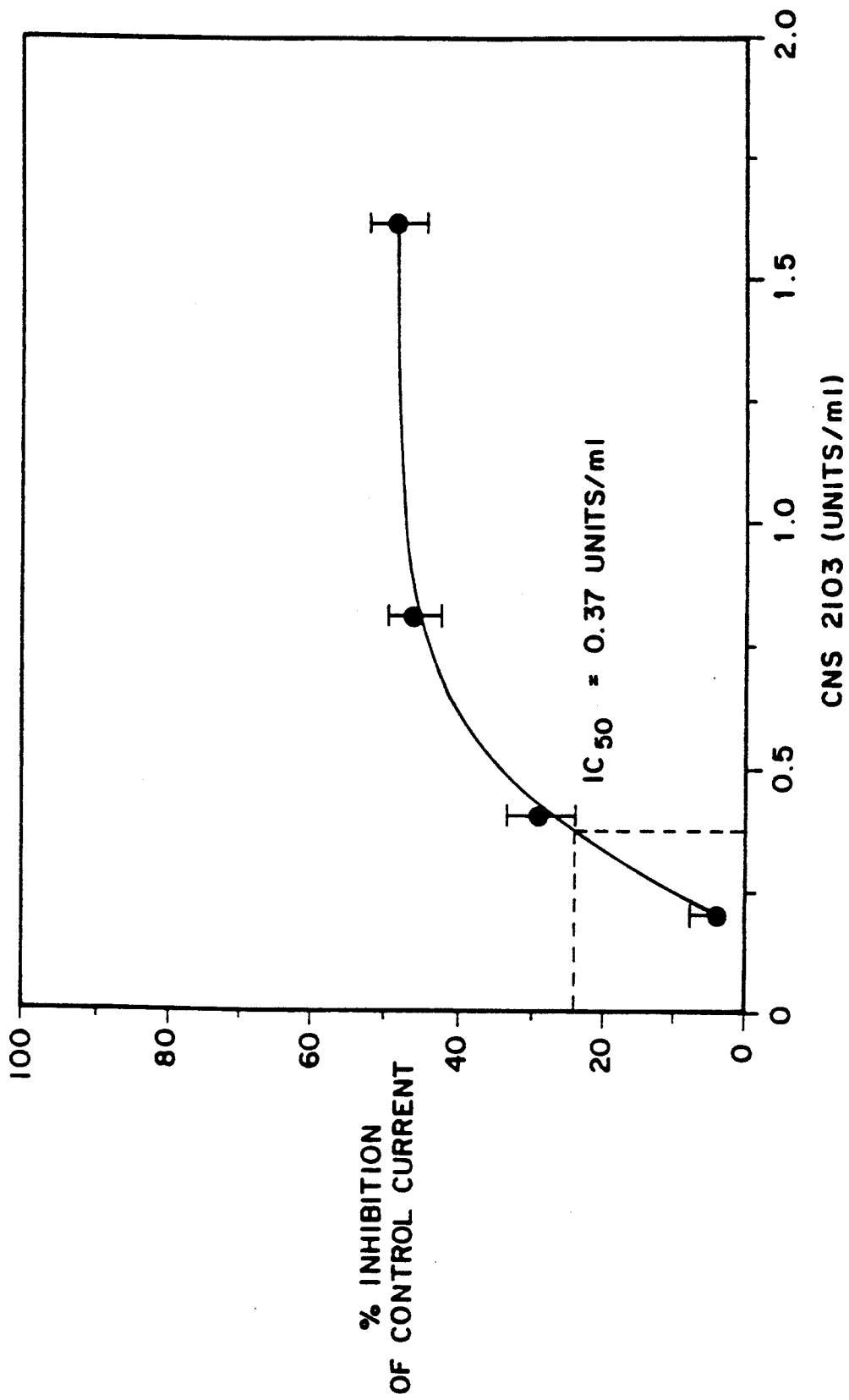
FIG. 12 is a graph showing that DOC1 can block up to 45% of the high-threshold current remaining during nimodipine treatment of N1E-115 cells.

As shown in FIG. 12, DOC1 blocked a maximum of 45% of the high-threshold current remaining after treatment with nimodipine. The concentration yielding half-maximal inhibition was 0.37 U/ml.

Summary of Salient Properties of DOC1

Summarized in the Table below are results of experiments designed to study the effect of DOC1 on calcium channels by calcium 45 uptake measurement and electrophysiological method, both of which are described above.

As shown, DOC1 exhibits a high degree of selectivity (on the order of two log units) for Ca versus Na currents. Notably, at concentrations that produce a substantial block of dihydropyridine resistant (R-type) Ca currents, no block of putative T-type channels was observed. Thus, it appears that DOC1 may be a selective blocker of high-threshold, slowly inactivating Ca channels with a broader spectrum of efficacy than nimodipine.

The implications of this pharmacological profile are that such a compound (if it is able to enter the brain) may, in addition to producing cerebral vasodilation, also directly block a greater proportion of Ca channel-mediated Ca entry into nerve cell bodies than nimodipine. For this reason it may have a competitive advantage over a dihydropyridine in prevention of neuronal Ca overload.

The striking specificity of DOC1 for Ca channels over Na or K channels is illustrated below.

| Summary of Properties of DOC1 | |
|---|---|
| Property | IC$_{50}$, units/ml |
| Block of DHP-snsitive L-type channels, | |
| GH$_4$C$_1$ clonal pituitary cells, $^{45}$Ca uptake | 0.4–1.5* |
| GH$_4$C$_1$ clonal pituitary cells, electrophysiol | 1.5 (puff) |
| Block of K-stimulated $^{45}$Ca uptake (L-channels?) Cortical neurons | 0.1–0.4** |
| Block of DHP-resistant R-channels, N1E-115 cells (electrophys) | 0.4 |
| Block of low threshold, inactivating (T?) channels, N1E-115 cells (electrophysiol) | none |
| Block of Na current, N1E-115 cells | not signif. |
| Block of K currents, N1E-115 cells | (12% @ 1 U/ml) |

*consistent inhibitory effects; IC$_{50}$ varied among GH$_4$C$_1$ cultures
**some cultures of cortical neurons appeared insensitive to both DOC1 and dihydropyridines; IC$_{50}$ varied among sensitive cultures

Advantages of Screening Compounds which Affect Trans-Membrane Transport by the Microscreen Uptake Method Certain scarce natural products and synthetic compounds are available in limited quantity and may be very expensive. In order to precisely and quantitatively identify therapeutically relevant biological activities among these sources with maximum economy, it is desirable to have an assay system that can obtain a maximal amount of information from a minimum amount of material. In addition, to screen and evaluate large chemical libraries of compounds efficiently, the screening assay system should be a "high throughput" system, capable of evaluating many compounds per miniday.

In principle, radioligand binding assays are capable of high throughput in screening compounds which affect transport of molecules or ions into the cells, organelles or membrane vesicles. Since such assays are based on binding of a radioligand to a known receptor, however, those novel drugs which interact with distinct receptor sites not previously recognized will not be identified by such a screening method. Furthermore, it is often impossible to infer from radioligand binding studies alone what the functional effects of a compound would be when it occupies such a binding site, i.e., will it potentiate or antagonize the normal biological response?

In certain instances, properly designed functional assays may consume minimal amounts of compounds to be evaluated (e.g., electrophysiological approaches for identifying ion channel antagonists); however, such functional assays are not in general capable of high throughput.

The above considerations led to the development of a microscreen uptake screening method, a novel approach for new drug discovery. Advantages of this screening method are as follows:

(1) Minimal Consumption of Material

By employing a strategy in which the assay is performed in very small volumes (typically less than 25 μl and can be as little as about 8 μl, as shown above in identifying DOC1 and DOC3), minimal amounts of material are consumed.

(2) Direct Resolution of Therapeutically Relevant Function

To identify modifiers of ion channels, ion pumps, or other transport systems in cell membranes, radioisotopes of the molecules actually translocated by said transport systems are employed. The assay is designed to identify and quantify the nature of the effect of compounds of interest on said transport systems.

In the current example, we performed experiments to study the effect of DOC1 on the selective binding of [$^3$H]nimodipine to the dihydropyridine binding sites on the L-type calcium channels in rat brain membranes. Other compounds which act through the same binding site as the dihydropyridines will inhibit this [$^3$H]nimodipine binding. Results of our experiments (not illustrated) showed that DOC1 had no significant inhibition of [$^3$H]nimodipine binding when added to the assay at a concentration of up to 0.6 units/ml. In the same experiments, nifedipine, a dihydropyridine compound similar to nifedipine, showed potent inhibition of the [$^3$H]nimodipine binding, giving 50% inhibition at about 20 nM. For related experimental results, see FIGS. 11A and 11B and FIG. 12 and the accompanying texts thereof.

The fact that, when used at concentrations well above those required for inhibition of L- and R-type channels, there is no inhibition of nimodipine binding to L-type channels supports the argument that DOC1 acts at a distinct, unique site on its calcium channel target. It also demonstrates that DOC1, which was identified by our screening assay system, would not have been discovered by this sort of conventional radioligand binding assay system, thus pointing out the particular advantages of the screening approach taught by the present invention.

(3) High Throughput

The assay system is designed so that large quantities (dozens or more) of candidate compounds can be evaluated per day. The physical manipulations involved in said assays resemble in simplicity and repetitiveness the sort of manipulations undertaken, for example, in performing radioligand binding assays to membrane-bound receptor sites. In many instances, the screening assays can be automated using much the same machinery employed in automating radioligand binding assays.

Two embodiments, among others, of this screening method are described above, namely, (a) an assay for antagonists of L-type (cardiovascular and neuronal) calcium channels of clonal pituitary cells (GH$_4$C$_1$), and (b) an assay for antagonists of presynaptic calcium channels controlling neurotransmitter release from organelles, i.e., brain nerve terminals (synaptosomes). Both assays were used to help discover and characterize DOC1 and DOC3.

Other variations of this approach include a screening assay employing suspensions of cells grown on beads. This may be desired since certain therapeutically relevant targets for drug discovery are not found on cells or organelles that are easy to grow or manipulated in free suspension. For example, neuronal cells in culture extend fragile processes which are easily ruptured, and for this reason such cells must be grown on a stable solid support. By growing such cells (e.g., neuroblastoma cell lines) on beads, the cells can freely extend processes which adhere to the beads, preventing them from damage while they are manipulated in suspension in a manner that otherwise resembles the manipulations of GH$_4$C$_1$ cells and synaptosomes as described above.

Alternatively, one may perform this screening assay employing suspensions of cells grown in hollow fibers for the same rationale as set forth above. As an example, cells can be grown in hollow fiber bundles. Individual hollow fibers can be snipped off from the bundle, ligated, and employed in radioisotopic flux studies.

By the same token, it may be desirable to conduct a screening assay employing cells grown on filters or other microporous media to provide a stable solid support. The radioisotopic flux assay can be performed in situ on a small portion of the filter, that portion of the filter can be placed on a larger filter acting as a "carrier", and extracellular isotope can be removed by filtration.

Use of the Claimed Compounds

DOC1, DOC3 and their analogs, either produced from natural sources or prepared by synthetic methods, can be used for the in vivo treatment of conditions characterized by inappropriate or excessive calcium influx into cells, such as stroke, brain trauma, hypertension, angina pectoris and the like. When target cells are central neuronal cells, it is preferable that the compound be acylated to increase its permeability through the blood-brain barrier.

Alternatively, these compounds can be used as immunogens for preparation of antibodies against venom from arachnids. Further, they can also be used as probes in studying the function and structure of various types of calcium channels.

When these compounds are used as drugs, the amount to be administered will, of course, depend upon the severity of the condition being treated, the route of administration chosen, and the specific activity of the compound, and ultimately will be decided by the attending physician or veterinarian. Such amount of the active compound as determined by the attending physician or veterinarian is referred to herein as an "therapeutically-effective" amount. For example, when a spider toxin with a molecular weight about 200 to 1,000 Da was used as an anticonvulsant, 2 $\mu$M/kg was administered intravenously [Jackson H., et al. (1989) Ann. Rev. Neurosci. 12:405].

The active compound may be administered by any route appropriate to the condition being treated. Preferably, the compound is injected into the bloodstream of the mammal being treated. It will be readily appreciated by those skilled in the art that the preferred route will vary with the condition being treated.

While it is possible for the active compound to be administered as the pure or substantially pure compound, it is preferable to present it as a pharmaceutical formulation or preparation. The formulations of the present invention, both for veterinary and for human use, comprise an active compound of the invention, as above described, together with one or more pharmaceutically acceptable carriers therefor, and optionally other therapeutic ingredients. The carrier must be "acceptable" in the sense of being compatible with the other ingredients of the formulation and not deleterious to the recipient thereof. Desirably, the formulation should not include substances with which indole-containing compounds or polyamine compounds are known to be incompatible.

The formulations may conveniently be presented in unit dosage form and may be prepared by any of the methods well known in the art of pharmacy. All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for parenteral administration conveniently comprise sterile aqueous solutions of the active ingredient with solutions which are preferably isotonic with the blood of the recipient. Such formulations may be conveniently prepared by dissolving solid active ingredient in water to produce an aqueous solution, and rendering said solution sterile. The formulation may be presented in unit or multi-dose containers, for example, sealed ampoules or vials.

Other Embodiments

The foregoing description has been limited to specific embodiments of this invention. It will be apparent, however, that variations and modifications may be made to the invention, with the attainment of some or all of the advantages of the invention.

For example, other components, such as peptides, have been identified in venom of *Dolomedes okefenokiensis*. Some of these compounds, by an action similar to that of DOC1 and DOC3, also show calcium channel blocking activity and are within the scope of the present invention. In addition, synthetic compounds which have structures that represent variations on the DOC1 and DOC3 polyamine structure are expected to function in a manner similar to DOC1 and DOC3, and are within the scope of the invention.

Other embodiments are within the following claims.

What is claimed is:

1. A compound of the formula:

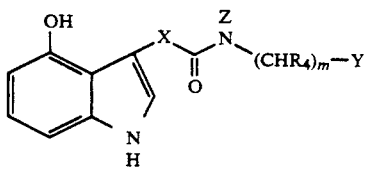

wherein each $R_4$, independently, is H or $C_{1-6}$ alkyl;

X is $CH_2$, $CH_2CH_2$, $CH=CH$, or $CH_2CH_2CH_2$;

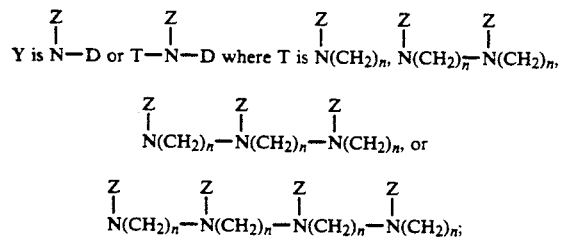

each Z, independently, is H, $CH_3$, or Q where Q is acyl, benzoyl, phenacetyl, benzyloxycarbonyl, alkoxycarbonyl, or N-methyl-dihydropyridine-3-carbonyl;

D is H or

where $R_5$ is H or $C_{1-4}$ alkyl;

m is an integer from 2 to 12, inclusive; and each n, independently, is an integer from 2 to 12, inclusive.

2. The compound of claim 1, wherein $R_1$ is H, $CH_3$, $CF_3$, F, Cl, Br, I, OH, $NH_2$, $NO_2$, $CONH_2$, or $SO_2NH_2$.

3. The compound of claim 1, wherein $R_2$ is H, $CH_3$, $CF_3$, F, Cl, Br, I, OH, $NH_2$, $NO_2$, $CONH_2$, or $SO_2NH_2$.

4. The compound of claim 1, wherein $R_3$ is H, $CH_3$, or $CONH_2$.

5. The compound of claim 1, wherein $R_4$ is H, $CH_3$, $C_2H_5$, $C_3H_7$, or $C_4H_9$.

6. The compound of claim 1, wherein X is $CH_2$, $CH=CH$, $CH_2CH_2$, or $CH_2CH_2CH_2$.

7. The compound of claim 1, wherein Z is H or $CH_3$.

8. The compound of claim 1, wherein $R_1$ is OH; each of $R_2$, $R_3$, $R_4$, and Z is H; m is 3 or 5;

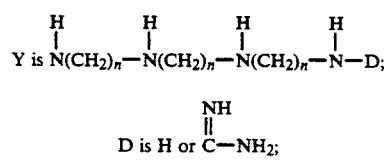

and each n, independently, is 3, 4, or 5.

9. The compound of claim 1, wherein m is 8, 10, or 12; and Y is

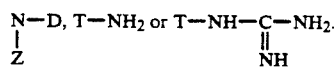

10. The compound of claim 1, wherein Q is acyl or benzoyl.

11. The compound of claim 1, wherein Q is phenacetyl, benzyloxycarbonyl, or alkoxycarbonyl.

12. The compound of claim 1, wherein Q is N-methyl dihydropyridine-3-carbonyl linked to N by an amide bond.

13. The compound of claim 1, wherein each of $R_3$ and $R_4$ is H; X is $CH_2$; Y is $T-NH_2$; m is 3, 4, or 5; and each n, independently, is 3, 4, or 5.

14. The compound of claim 13, wherein $R_1$ is OH, $R_2$ is H, and each Z is H.

15. The compound of claim 14, wherein m is 3 or 5 and each n, independently, is 3 or 5.

16. The compound of claim 15 of the formula:

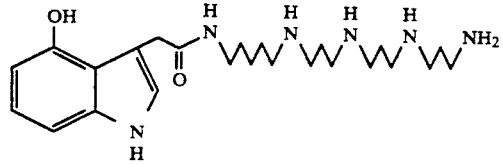

17. The compound of claim 15 of the formula:

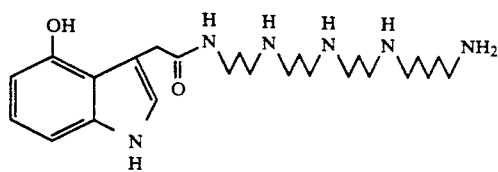

18. The compound of claim 1, wherein m is 8, 10, or 12; and Y is NH₂ or 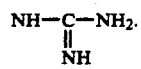
19. A pharmaceutical composition comprising a therapeutically-effective amount of the compound of claim 1 in a pharmaceutically-acceptable vehicle.
* * * * *

UNITED STATES PATENT AND TRADEMARK OFFICE
CERTIFICATE OF CORRECTION

PATENT NO.   : 5,312,928

DATED        : May 17, 1994

INVENTOR(S)  : Stanley M. Goldin et al.

It is certified that error appears in the above-identified patent and that said Letters Patent is hereby corrected as shown below:

Title page, under "OTHER PUBLICATIONS", page 2, column 1, "Adams...et al.", correct the spelling of "Activities";

Col. 2, line 21, replace "$\mu 3]$" with --823--;

Col. 3, line 38, replace "$CH_2$" with --$CH_3$--;

Col. 11, line 68, replace "18 ppm" with --1.8 ppm--.

Signed and Sealed this

Twenty-second Day of August, 1995

Attest:

BRUCE LEHMAN

Attesting Officer          Commissioner of Patents and Trademarks